United States Patent
Singh et al.

(10) Patent No.: US 6,737,438 B2
(45) Date of Patent: May 18, 2004

(54) SUBSTITUTED 1,2,4-TRIOXANES USEFUL AS ANTIMALARIAL AGENTS AND A PROCESS FOR THE PREPARATION THEREOF

(75) Inventors: Chandan Singh, Uttar Pradesh (IN); Pallvi Tiwari, Uttar Pradesh (IN); Sunil Kumar Puri, Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/113,205

(22) Filed: Mar. 28, 2002

(65) Prior Publication Data

US 2004/0053991 A1 Mar. 18, 2004

(51) Int. Cl.[7] ............ A61K 31/335; C07D 317/00; C07D 319/06; C07D 323/06
(52) U.S. Cl. ............ 514/452; 549/333; 549/336; 549/368
(58) Field of Search ............... 549/368, 336, 549/333; 514/452

(56) References Cited

FOREIGN PATENT DOCUMENTS

FR  2290892  6/1976

OTHER PUBLICATIONS

Daniel L. Klayman "Qinghaosu (Artemisinin): An Antimalarial Drug from China" Amer. Association Adv. Science, vol. 228 (1985) pp. 1049–1055.

Xuan–De Luo and Chia–Chiang Shen "The Chemistry, Pharmacology, and Clinical Applications of Qinghaosu (Artemisinin) and Its Derivatives" Medical Research Review, vol. 7, No. 1, (1987) pp. 29–52.

Syed S. Zaman and Ram P. Sharma "Some Aspects Of The Chemistry And Biological Activity Of Artemisinin and Related Antimalarials" Heterocycles vol. 32, No. 8, (1991) pp. 1593–1638.

Anthony R. Butler and Yu–Lin Wu "Artemisinin (Qinghaosu): A New type of Antimalarial Drug" Chemical Society Reviews, vol. 21, No. 2, (1992) pp. 85–146.

Meshnick et al. "Artemisinin and the Antimalarial Endoperoxides: From Herbal Remedy to Targeted Chemotherapy" Americal Society of Microbiology Reviews vol. 60, No. 2, (1996) pp. 301–315.

Asish K. Bhattacharya and Ram P. Sharma "Recent Developments On The Chemistry and Biological Activity Of Artemisinin And Related Antimalarials an Update" Heterocycles vol. 51, No. 7, (1999) pp. 1679–1745.

Richard K Haynes and Simone C. Vonwiller "Form qinhao, Marvelous Herb of Antiquity, to the Antimalarial Trioxane Qinghaosu—and Some Remarkable New Chemistry" American Chemical Society vol. 30, No. 2, (1997) pp. 73–79.

Cumming et al. "Antimalarial Activity of Artemisinin (Qinghaosu) and Related Trioxanes: Mechanism(s) of Action" Advances in Pharmacology, vol. 37, (1997) pp. 253–297.

Chandan Singh, "Preparation of B–Hydrocyhydroperoxides by Photoosygenation of Allylic Alcohols and Their Elaboration Into 1, 2, 4–Trioxanes" Tetrahedron Letters vol. 31, No. 47 (1990) pp. 6901–6902.

Chandan Singh et al. "Synthesis Of In Vivo Patent Antimalarial 1, 2, 4–Trioxanes" Bioorganic & Medicinal Chemistry Letters, vol. 2, No. 5, (1992) pp. 497–500.

Chandan Singh et al. "In Vivo Potent Antimalarial 1,2, 4–Trioxanes: Synthesis and Activity Of 8–(α–Arylvinyl)–6, 7,10–Trioxaspiro[4,5] Decanes and 3–(α–Arylvinyl)–1,2, 5–Trioxaspiro [5,5] Undecanes Against Plasmodium Berghei in Mice" Bioorganic & Medicinal Letters, vol. 5, No. 17, (1995) pp. 1913–1916.

*Primary Examiner*—Alan L. Rotman
*Assistant Examiner*—Raymond Covington
(74) *Attorney, Agent, or Firm*—Morgan & Finnegan, LLP (57) ABSTRACT

In the present invention relates to a novel series of antimalarial 1,2,4-trioxanes analogues of general formula 7,

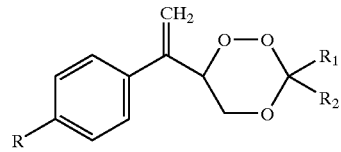

7 wherein R represents cycloalkyl groups selected from the groups consisting of cyclopentyl, cyclohexyl, cycloheptyl and cyclooctyl or aryl groups selected from phenyl, 4-bromophenyl and 4-chlorophenyl, $R_1$ and $R_2$ represent hydrogen, alkyl group selected from methyl, ethyl, propyl and decyl, aryl selected from phenyl or parts of a cyclic systems such as cyclopentane, cyclohexane, substituted cyclohexane, cycloheptane bicyclo(2.2.1)heptane, adamantane and its preparation thereof; several of these novel compounds show promising antimalarial activity against multidrug resistant malaria in mice.

13 Claims, No Drawings

SUBSTITUTED 1,2,4-TRIOXANES USEFUL AS ANTIMALARIAL AGENTS AND A PROCESS FOR THE PREPARATION THEREOF

FIELD OF THE INVENTION

The present invention relates to a novel series of antimalarial 1,2,4-trioxanes analogues of general formula 7,

7 wherein R represents cycloalkyl groups selected from the groups consisting of cyclopentyl, cyclohexyl, cycloheptyl and cyclooctyl or aryl groups selected from phenyl, 4-bromophenyl and 4-chlorophenyl, $R_1$ and $R_2$ represent hydrogen, alkyl group selected from methyl, ethyl, propyl and decyl, aryl selected from phenyl or parts of a cyclic systems such as cyclopentane, cyclohexane, substituted cyclohexane, cycloheptane bicyclo(2.2.1)heptane, adamantane and its preparation thereof; several of these novel compounds show promising antimalarial activity against multidrug resistant malaria in mice.

BACKGROUND OF INVENTION

Malaria, endemic in many parts of the tropical countries, with approximately 300–500 million episodes of clinical infection and nearly 2 million deaths per year worldwide, is a serious health problem. The rapid emergence of resistance by *Plasmodium falciparum* to the existing therapies, e.g. chloroquine, mefloquine etc, has added new dimensions to this problem. Against this background discovery of artemisinin 1, a sesquiterpene lactone endoperoxide, isolated from the Chinese traditional herbal remedy against malaria, Artemisia annua, has been a welcome development in the chemotherapy of malaria. Some of the semisynthetic derivatives of artemisinin e.g. artemether 2, arteether 3, and artesunic acid 4 are more active than artemisinin and are currently being used clinically. These drugs are effective against both chloroquine sensitive and chloroquine resistant strains of *Plasmodium falciparum* [For reviews on artemisinin and its derivatives, see: (a) Klayman, D. L. *Science*, 1985, 228, 1049; (b) Luo, X. D.; Shen, C. C. *Med. Res. Rev.*, 1987, 7, 29; (c) Zaman, S. S.; Sharma, R. P. *Heterocycles*, 1991,32,1593; (d) Butler, A. R.; Wu, Y. Lin. *Chem. Soc. Rev.*, 1993, 21,85; (e) Meshnick, S. R.; Taylor, T. E.; Kamchonwongpaisan, S. *Microbiol. Rev.*,1996, 60,301; (f) Bhattacharya, A. K.; Sharma, R. P. *Heterocycles*,1999, 51, 1681; (g) Haynes, R. K.; Vonwiller, S. C. *Acc. Chem. Res.*, 1997, 73].

1

2

3

4

The limited availability of artemisinin from natural sources and the realization that 1,2,4-trioxane is the pharmacophore for the antimalarial activity of artemisinin and its analogues, has inspired major efforts towards the preparation and bioevaluation of structurally simple synthetic 1,2,4-trioxanes. As a result of these efforts, a number of methodologies have been developed by various workers for the preparation of 1,2,4-trioxanes (prototypes of these trioxanes are given in FIG. 1). Several of these synthetic trioxanes have shown promising antimalarial activities both in vitro and in vivo [Cumming, J. M.; Ploypradith, P.; Posner, G. H. *Adv Pharmacol*, 1999, 37,253].

Figure 1:
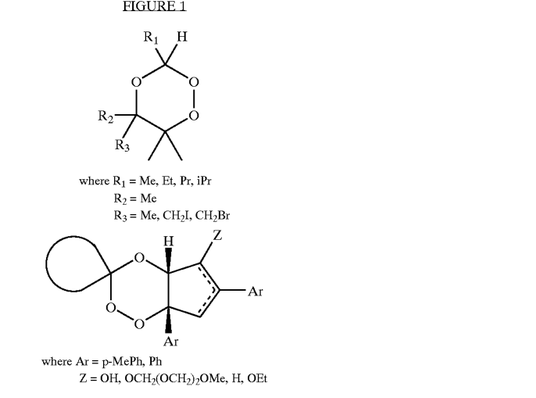

FIGURE 1 where $R_1$ = Me, Et, Pr, iPr
$R_2$ = Me
$R_3$ = Me, $CH_2I$, $CH_2Br$ where Ar = p-MePh, Ph
Z = OH, $OCH_2(OCH_2)_2OMe$, H, OEt where Z = PO(OPh)₂
Z = CH₂Ph Singh et al. have prepared 1,2,4-trioxanes by the regiospecific photooxygenation of allylic alcohols to furnish -hydroxyhydroperoxide, which on condensation with aldehyde or ketone in the presence of an acid catalyst furnish 1,2,4-trioxane [(a) Singh, C. Tetrahedron Lett. 1990,31, 6901;(b) Singh, C.; Misra, D.; Saxena, G.; Chandra, S. Bioorg. Med. Chem. Lett.,1992, 2, 497; Singh, C.; Misra, D.; Saxena, G.; Chandra, S. Bioorg. Med. Chem. Lett., 1995,17, 1913]. As an extension of this work we have prepared a new series of novel 1,2,4-trioxanes which have been found to be highly active against multi-drug resistant P. yoelii in mice and which are the subject matter of this patent. This invention relates to novel substituted 1,2,4-trioxanes useful as antimalarial agents.

This invention also relates to a process for the preparation of novel substituted 1,2,4-trioxanes.

This invention particularly relates to a process for the preparation of 6-[(cycloalkylphenyl/Substituted biphenyl)vinyl]-1,2,4-trioxanes, a new series of antimalarial agents. More particularly the present invention provides a process for the preparation of 1,2,4-trioxanes of general formula 7 wherein R represents cycloalkyl groups selected from the groups consisting of cyclopentyl, cyclohexyl, cycloheptyl and cyclooctyl or aryl groups selected from phenyl, 4-bromophenyl and 4-chlorophenyl, $R_1$ and $R_2$ represent hydrogen, alkyl group selected from methyl, ethyl, propyl and decyl, aryl selected from phenyl, or part of a cyclic system such as cyclopentane, cyclohexane, substituted cyclohexane, cycloheptane, cyclo(2.2.1)heptane, adamantane. These trioxanes are new compounds and are useful as antimalarial agents. Some of these compounds have been tested against multi-drug resistant malaria in mice and have shown promising antimalarial activity. The invention, thus relates to pharmaceutical industry.

The trioxanes of the general formula 7 are new chemical entities and they have not been prepared earlier.

The main objective of the present invention is to provide novel substituted 1,2,4-trioxanes.

The objective of the present invention is also to provide a process for the preparation of novel substituted 1,2,4-trioxanes of general formula 7, a new series of antimalarial agents. Accordingly, the present invention provides a process for the preparation of novel substituted 1,2,4-trioxanes of general formula 7 as given below.

Wherein R represents cycloalkyl groups selected from the groups consisting of cyclopentyl, cyclohexyl, cycloheptyl and cyclooctyl or aryl groups selected from phenyl, 4-bromophenyl and 4-chlorophenyl, $R_1$ and $R_2$ represent hydrogen, alkyl group selected from methyl, ethyl, propyl and decyl, aryl selected from phenyl or parts of a cyclic systems such as cyclopentane, cyclohexane, substituted cyclohexane, cycloheptane, bicyclo (2.2.1)heptane, adamantane which comprises reacting aryl methyl ketone of formula 1, wherein R represents cycloalkyl groups selected from the groups consisting of cyclopentyl, cyclohexyl, cycloheptyl or cyclooctyl or aryl groups selected from phenyl, 4-bromophenyl and 4-chlorophenyl with haloacetate such as ethyl bromoacetate or ethylchloroacetate and Zn in presence of catalytic amount of $I_2$ in an aprotic organic solvent at a temperature range of room temperature to refluxing temperature to give β-hydroxyester of formula 2, wherein R has the same meaning as above, dehydrating the above said β-hydroxy esters of formula 2 using a catalyst selected from the group consisting of $I_2$, $P_2O_5$, PTSA and cation exchanger such as Amberlyst-15, in an aprotic organic solvent at room temperature to refluxing temperature to obtain α,β-unsaturated ester 3, wherein R has the same meaning as above, reducing the above said esters of formula 3 with a metal hydride such as $LiAlH_4$ in an ether solvent at a temperature ranging from 0° C. to refluxing temperature to give allylic alcohols of the formula 4, wherein R has the same meaning as above, photooxygenating the above said allylic alcohols of formula 4 in presence of a sensetizer in an organic solvent at temperature ranging from −10° C. to room temperature to obtain β-hydroxyhydroperoxides of formula 5, wherein R has the same meaning as above , reacting in situ or after isolating the β-hydroxyhydroperoxide of the formula 5 with an aldehyde or ketone of the general formula 6, wherein, $R_1$ and $R_2$ represent hydrogen, alkyl group such as methyl, ethyl, propyl and decyl, aryl such as phenyl and parts of a cyclic system selected from groups consisting of cyclopentane, cyclohexane, cycloheptane, substituted cyclohexanes, bicyclo(2.2.1)heptane, adamantane, in presence of an acid catalyst in an aprotic organic solvent at a temperature range of 0° C. to room temperature, followed by isolation and purification by known methods to furnish the trioxanes of general formula 7, wherein R, $R_1$ and $R_2$ have the same meaning as above.

In the process aryl methyl ketone of formula 1 are reacted with haloacetate such as ethyl bromoacetate or ethylchloroacetate and Zn in presence of catalytic amount of $I_2$ in an aprotic organic solvent such as benzene, toluene, diethyl ether, THF to furnish β-hydroxy ester of formula 2.

These β-hydroxy esters of formula 2 can be isolated and purified by standard laboratory methods such as column chromatography or crystallization or can be used without purification in the next step. β-Hydroxy esters of formula 2 except compound 2e (formula 2, R=Ph) are new compounds and they have not been prepared earlier. β-Hydroxy ester 2e (formula 2, R=Ph) is a known compound [Farmaco. Ed. Sci 1978,33(12), 992–8 (Ital)].

In the process dehydration of β-hydroxy esters of formula 2 may be effected in aprotic organic solvent such as benzene, toluene, CHCl$_3$ in the presence of a dehydrating catalysts selected from I$_2$, P$_2$O$_5$, p-toluene sulfonic acid, H$_2$SO$_4$ or Amberlyst-15 (cation exchanger) to furnish α,β-unsaturated esters of formula 3. These unsaturated esters can be isolated and purified by standard laboratory methods such as column chromatography or crystallization. The α,β-unsaturated esters of formula 3 except compound 3e (formula 3, R=Ph) are new compounds and they have not been prepared earlier. α,β-unsaturated ester of formula 3e (formula 3, R=Ph) is a known compound [*Chemical Abstract*, 1976, 86, P106177d].

In the process reduction of α,β-unsaturated esters of formula 3 is effected with a complex metal hydride such as LiAlH$_4$ in an ether solvent such as diethyl ether, tetrahydrofuran, to furnish allylic alcohol of the formula 4. These allylic alcohols of formula 4 can be isolated and purified by standard laboratory methods such as crystallization or column chromatography. The allylic alcohols of formula 4 are new compounds and they have not been prepared earlier.

In the process photooxygenation of allylic alcohols of formula 4 may be effected by passing oxygen gas or air in the solution of the alcohol in an organic solvent and in the presence of a dye and a light source which provides visible light for a period in the range of 2 to 5 h, to furnish β-hydroxyhydroperoxides of formula 5. These β-hydroxyhydroperoxide of formula 5 which are new chemical entities can be isolated and purified by standard laboratory methods such as crystallization or column chromatography or can be used in situ, without purification, in the next step. The dye which acts as a sensitizer i.e. converts $^3$O$_2$ to highly reactive $^1$O$_2$, may be selected from methylene blue, Rose Bengal, tetraphenylporphine and the like. Organic solvent used may be selected from CH$_2$Cl$_2$, benzene, CH$_3$CN, acetone, ethanol and the like.

In the process reaction of β-hydroxyhydroperoxide of formula 5 with aldehyde/ketones of formula 6 is done in an aprotic solvent in the presence of an acid catalyst to furnish trioxanes of formula 7. The aldehyde and ketones used may be such as benzaldehyde, acetone, ethyl methyl ketone, methyl propyl ketone, decyl methyl ketone, cyclopentanone, cyclohexanone, and bicyclic ketone such as norcamphor and tricyclic ketones such as 2-adamantanone. The acid catalyst used may be such as HCl, p-toluenesulfonic acid, H$_2$SO$_4$, acidic resin like Amberlyst-15. The aprotic solvents used may be such as CH$_2$Cl$_2$, CHCl$_3$, benzene, CH$_3$CN. These trioxanes of formula 7 can be isolated and purified by standard laboratory methods such as column chromatography and crystallization. These trioxanes are new chemical entities and they have not been prepared earlier. Some of the trioxanes of formula 7 have been tested against malarial parasites in mice and show promising antimalarial activity.

The invention is further illustrated by the following examples which should not, however, be construed to limit the scope of the present invention.

EXAMPLE 1

Ethyl 3-Hydroxy-3-(4'-Cyclopentylphenyl)-Butanoate (Compound 2a, Formula 2, R=Cyclopentyl)

To a refluxing mixture of 4'-cyclopentylacetophenone (17 g), I$_2$ (5 mg) and Zn dust (12 g) in benzene (150 ml) was added ethylbromoacetate (11 ml) dropwise over 30 minutes. The mixture was refluxed for next 45 min and then cooled to room temperature. It was acidified with 10% aqueous HCl solution (150 ml) and organic layer was separated out. The organic layer was washed with water, dried (Na$_2$SO$_4$) and concentrated. The crude product was purified by column chromatography on silica gel to furnish 22 g (88.1% yield) of ethyl 3-hydroxy-3-(4'-cyclopentylphenyl)-butanoate (2a) as oil.

Ethyl 3-(4'-Cyclopentylphenyl)-But-2-Enoate (Compound 3a, Formula 3, R=Cyclopentyl)

To a solution of ethyl 3-hydroxy-(4'-cyclopentylphenyl)-butanoate (2a, 12 g) in benzene (150 ml) was added p-toluenesulfonic acid and refluxed for 1 h. The mixture was diluted with sat. NaHCO$_3$ (100 ml) and organic layer was separated. The organic phase was washed with water, dried (Na$_2$SO$_4$) and concentrated. The crude product was purified by column chromatography on silica gel to give 8.9 g (79.4% yield) of ethyl 3-(4-cyclopentylphenyl)-but-2-enoate (3a, formula 3, R=cyclopentyl) as oil.

3-(4'-Cyclopentylphenyl)-2-Butenol (Compound 4a, Formula 4, R=Cyclopentyl)

To an ice cooled slurry of LiAlH$_4$ (2.7 g) in dry ether (150 ml) was added a solution of ethyl 3-(4'-cyclopentylphenyl)-but-2-enoate (3a, 8.2 g) in dry ether (50 ml) dropwise. The mixture was stirred at 0° C. for 3 h. The reaction mixture was quenched with water (10 ml). A solution of 10% NaOH (5 ml) was added and then ether layer was decanted. The precipitate was washed with ether and combined organic layer was concentrated. The crude product was purified by column chromatography on silica gel to give 5.6 g (82.3% yield) of 3-(4'-cyclopentylphenyl)-2-butenol (4a, formula 4, R=cyclopentyl) as oil.

3-(4'-Cyclopentylphenyl)-1-Hydroxy-But-3-En-2-Hydroperoxide (Compound 5a, Formula 5, R=Cyclopentyl)

A solution of 3-(4'-cyclopentylphenyl)-2-butenol (4a, 500 mg) and methylene blue (5 mg) in CH$_2$Cl$_2$ (30 ml) was irradiated with a 250-watt tungsten-halogen lamp at –10° C. while oxygen was passed through the reaction mixture for 5 h. The reaction mixture was concentrated under reduced pressure at r.t. and purified by column chromatography on silica gel to furnish 0.29 g (51.7% yield) of hydroperoxide 5a as a solid m.p. 95–97° C. 8-[(4'-Cyclopentylphenyl) Vinyl]-6,7,10-Trioxaspiro-[4,5]-Decane (Trioxane 7aa, Formula 7, R=Cyclopentyl; R$_1$R$_2$=—CH$_2$CH$_2$CH$_2$CH$_2$)

A solution of 3-(4-cyclopentylphenyl)-2-butenol (4a, 500 mg) and methylene blue (5 mg) in CH$_3$CN (30 ml) was photooxygenated at –10° C. for 3 h. Cyclopentanone (1.5 ml) and p-toluenesulfonic acid (50 mg) were added and reaction mixture was left at r.t. for 20 h. Reaction mixture was concentrated to remove CH$_3$CN under reduced pressure, diluted with NaHCO$_3$ (5 ml) and water (50 ml), extracted with ether (3×50 ml), dried over Na$_2$SO$_4$ and concentrated. The crude product was purified by chromatotron on silica gel to furnish 0.38 g (52.7% yield based on allylic alcohol, 4a used) of trioxane 7aa as oil.

EXAMPLE 2

Trioxane 8a, Formula 8, R=Cyclopentyl

A solution of 3-(4-cyclopentylphenyl)-2-butenol (4a, 320 mg) and methylene blue (5 mg) in CH$_3$CN (25 ml) was photooxygenated at –10° C. for 4 h. Norcamphor (800 mg) and p-toluenesulfonic acid (60 mg) were added and reaction mixture was stirred for 20 h at r.t. The reaction mixture was worked up as above and concentrated. Crude product was purified by chromatotron on silica gel to furnish 0.14 g (28% yield based on allylic alcohol 4a, used) of trioxane 8a, m.p. 91–93° C.

EXAMPLE 3

Trioxane 9a, Formula 9, R Cyclopentyl

A solution of 3-(4'-cyclopentylphenyl)-2-butenol (4a, 500 mg) and methylene blue (5 mg) in $CH_3CN$ (30 ml) was photooxygenated at −10° C. for 3 h. 2-Adamantanone (500 mg) and p-toluenesulfonic acid (50 mg) were added and reaction mixture was stirred for 3.5 h at r.t. The reaction mixture was worked up as above and concentrated. Crude product was purified by chromatotron on silica gel to furnish 430 mg (49.4% yield, based on allylic alcohol, 4a used) of trioxane 9a, m.p. 74–76° C.

EXAMPLE 4

Trioxane 7ab, Formula 7, R=Cyclopentyl; $R_1R_2$=—$CH_2CH_2CH(Ph)CH_2CH_2$—

A solution of 3-(4'-cyclopentylphenyl)-2-butenol (4a, 500 mg) and methylene blue (5 mg) in $CH_3CN$ (30 ml) was photooxygenated at −10° C. for 3 h. 4-Phenylcyclohexanone (1 g) and p-toluenesulfonic acid (50 mg) were added and reaction mixture was stirred for 20 h at r.t. Reaction mixture was worked up as above and concentrated. Crude product was purified by chromatotron on silica gel to furnish 500 mg (60.2% yield, based on allylic alcohol, 4a used) of trioxane 7ab, m.p. 98–100° C.

EXAMPLE 5

Ethyl 3-Hydroxy-3-(4'-Cyclohexylphenyl)-Butanoate (Compound 2b, Formula 2, R=Cyclohexyl)

To a refluxing mixture of 4'-cyclohexylacetophenone (25 g), $I_2$ (5 mg) and Zn (17 g) in benzene (150 ml) was added ethylbromoacetate (20.7 ml) dropwise during 30 minutes. The mixture was refluxed for 2 h and then cooled to room temperature. It was acidified with 10% HCl (200 ml) an organic layer separated out. The organic phase was washed with water, dried ($Na_2SO_4$) and concentrated. The crude product was purified by column chromatography using $SiO_2$ as adsorbent and hexane-ethylacetate mixture as eluant to give 28 g (80% yield) of ethyl 3-hydroxy-3-(4-cyclohexylphenyl)-butanoate (2b, formula 2, R=cyclohexyl) m.p. 45° C.

The above compound was also prepared using different reaction condition. Table 1 gives the condition used and yield of compound 2b.

TABLE 1

| Solvent | Temperature | Reaction time | Yield |
| --- | --- | --- | --- |
| Diethyl ether | r.t. | No reaction | — |
| Diethyl ether | Refluxed | No reaction | — |
| Toluene | Refluxed | 30 minutes | 90% |

Ethyl 3-(4'-Cyclohexylphenyl)-But-2-Enoate (Compound 3b, R=Cyclohexyl)

To a solution of ethyl 3-hydroxy-3-(4'-cyclohexylphenyl)-butanoate (2b, 29.5 g) in benzene (80 ml) was added p-toluenesulfonic acid (1.8 g) and was refluxed for 2 h. The reaction mixture was diluted with sat. $NaHCO_3$, benzene layer separated out. The organic layer was washed with water, dried ($Na_2SO_4$) and concentrated. The crude product was purified by column chromatography on silica gel to give 12.7 g (46.01% yield) of ethyl 3-hydroxy-3-(4'-cyclohexylphenyl)-but-2-enoate (3b, formula 3, R=cyclohexyl) as oil.

The compound 3b was also prepared using different reaction condition. Table 2 gives the conditions used and the yield of compound 3b.

TABLE 2

| Acid catalyst | Solvent | Temperature | Reaction time | Yield (%) |
| --- | --- | --- | --- | --- |
| $P_2O_5$ | Toluene | Refluxed | 1 h | 65.2 |
| Amberlyst-15 | Toluene | Refluxed | 1 h | 35.1 |
| $I_2$ | Benzene | Refluxed | 1.5 h | 95.6 |
| $H_2SO_4$ | $CHCl_3$ | r.t. | 36 h | 29.0 |

3-(4'-Cyclohexylphenyl)-2-Butenol (Compound 4b, Formula 4, R=Cyclohexyl)

To an ice-cooled slurry of $LiAlH_4$ (3.8 g) in dry ether (200 ml) was added a solution of ethyl 3-(4'-cyclohexylphenyl)-but-2-enoate (3b, 12.7 g) in dry ether (50 ml) dropwise. The reaction mixture was stirred for 3 h at 0° C. The reaction mixture was quenched with water (20 ml). A solution of 10% NaOH (10 ml) was added and the ether layer was decanted. The precipitate was washed with ether and combined extracts were concentrated. The crude product was purified by column chromatography on silica gel as adsorbent and hexane/ethylacetate as eluant to furnish 9.5 g (88.7% yield) of 3-(4'-cyclohexylphenyl)-2-butenol (4b) m.p. 54–55° C.

The $LiAlH_4$ reduction of ethyl 3-(4'-cyclohexylphenyl)-but-2-enoate (3b) using THF as solvent under refluxing conditions did not provide the desired compound.

3-(4'-Cyclohexylphenyl)-1-Hydroxy-But-3-En-2-Hydroperoxide (Compound 5b, Formula 5, R=Cyclohexyl)

A solution of 3-(4'-cyclohexylphenyl)-2-butenol (4b, 600 mg) and methylene blue (20 mg) in acetonitrile (35 ml) was irradiation with a 250-watt tungsten-halogen lamp at −6° C. while oxygen was passed through the reaction mixture for 5 h. The crude product obtained by usual aqueous workup was crystallized from $CH_2Cl_2$ to give 80 mg of hydroperoxide 5b. The filtrate was chromatographed on silica gel to give 400 mg of hydroperoxide 5b. The combined yield of hydroperoxide (compound 5b, formula 5, R=cyclohexyl) was 480 mg (70% yield), m.p. 95–97° C.

Photooxygenation of 3-(4'-cyclohexylphenyl)-2-butenol (4b) in benzene at −6° C. using tetraphenylphorphine as sensitizer furnished the above hydroperoxide 5b in 85.2% yield.

3,3-Dimethyl-6-[4'-Cyclohexylphenyl]Vinyl-1,2,4-Trioxane (Trioxane 7ba, Formula 7, R=Cyclohexyl)

A solution of 3-(4'-cyclohexylphenyl)-2-butenol (4b, 500 mg) and methylene blue (50 mg) in acetone (30 ml) was photooxygenated at −6° C. for 3 h to give compound 5b (as shown by TLC). To the mixture was added p-toluenesulfonic acid (60 mg) and stirred for 3 h at r.t. The reaction mixture was worked up as above and concentrated. The crude product was purified by column chromatography on silica gel to furnish 500 mg (76.9% yield based on allylic alcohol, 4b used) of trioxane 7ba, m.p. 54–55° C.

EXAMPLE 6

3-Decyl,3-Methyl-6-[(4'-Cyclohexylphenyl)Vinyl]-1, 2,4-Trioxane (Trioxane 7bb, Formula 7, R= Cyclohexyl)

A solution of 3-(4'-cyclohexylphenyl)-2-butenol (4b, 500 mg) and methylene blue (5 mg) in $CH_3CN$ (30 ml) was photooxygenated at −6° C. for 3 h. 2-Dodecanone (1 ml) and p-toluenesulfonic acid were added and reaction mixture was stirred at r.t for 18 h. The reaction mixture was worked up as above and concentrated. The crude product was purified by chromatotron on silica gel to furnish 290 mg (31.1% yield, based on allylic alcohol, 4b used) of trioxane 7bb as oil.

EXAMPLE 7

6-[(4'-Cyclohexylphenyl)Vinyl]-3-Phenyl-1,2,4-Trioxane (Trioxane 7bc, Formula 7, R=Cyclohexyl]

A solution of 3-(4'-cyclohexylphenyl)-2-butenol (4b, 500 mg) and methylene blue (5 mg) in $CH_3CN$ (25 ml) was photooxygenated at −6° C. for 2.5 h. Benzaldehyde (1 ml) and p-toluenesulfonic acid (50 mg) were added and the mixture was left at r.t. for 18 h. Reaction mixture was worked up and crude product was purified by flash column chromatography on silica gel to furnish 340 mg (44.7% yield based on allylic alcohol, 4b used) of trioxane 7bc, m.p. 86–88° C.

EXAMPLE 8

3-[(4'-Cyclohexylphenyl)Vinyl]-1,2,5-Trioxaspiro(5, 5)Undecane (Trioxane 7bd, Formula 7, R= Cyclohexyl, $R_1R_2$=—$CH_2CH_2CH_2CH_2CH_2$—)

A solution of 3-(4'-cyclohexylphenyl)-2-butenol (4b, 500 mg) and methylene blue (5 mg) in $CH_3CN$ (30 ml) was photooxygenated at −6° C. for 3 h. Cyclohexanone (1.5 ml) and p-toluenesulfonic acid (50 mg) were added and the mixture was stirred for 4 h. The reaction mixture was worked up and crude product was purified by flash column chromatography on silica gel to furnish 550 mg (74.3% yield based on allylic alcohol, 4b used) of trioxane 7bd, m.p. 60–62° C.

EXAMPLE 9

Trioxane 8b, Formula 8, R=Cyclohexyl

A solution of 3-(4'-cyclohexylphenyl)-2-butenol (4b, 500 mg) and methylene blue (5 mg) in $CH_3CN$ (30 ml) was photooxygenated at −8° C. for 4 h. Norcamphor (1 ml) and p-toluenesulfonic acid (50 mg) were added and the mixture was left at 5° C. for 16 h. The reaction mixture was worked up and the crude product was purified by flash column chromatography on silica gel to furnish 300 mg (40.8% yield based on allylic alcohol, 4b used) of trioxane 8b, m.p. 70–71° C.

EXAMPLE 10

Trioxane 9b, Formula 9, R=Cyclohexyl

A solution of 3-(4'-cyclohexylphenyl)-2-butenol (4b, 500 mg) and methylene blue (5 mg) in $CH_3CN$ (50 ml) was photooxygenated at 6° C. for 3 h. 2-Adamantanone (1 g) and p-toluenesulfonic acid (50 mg) were added and reaction mixture was stirred at r.t. for 2 h. and then left unstirred at 5° C. for 15 h. Reaction mixture was worked up and crude product was purified by column chromatography on silica gel to furnish 500 mg (58.8% yield based on allylic alcohol, 4b used) of trioxane 9b, m.p. 75–76° C. Trioxane 9b was also prepared by the following method using purified hydroperoxide 5b.

To a solution of hydroperoxide 5b (290 mg) and 2-adamantanone (300 mg) in $CHCl_3$ (20 ml) was added one drop conc. $H_2SO_4$ and the reaction was kept at r.t.for 14 h. The reaction mixture was diluted with sat. $NaHCO_3$ (5 ml) and water (10 ml), extracted with ether (2×20 ml), dried over $Na_2SO_4$ and concentrated. The crude product was purified by chromatotron on silica gel to furnish 250 mg (49.0% yield) of trioxane 9b, m.p. 75–76° C.

The above trioxane was also prepared using different reaction conditions. Table 3 gives the conditions used and the yields of the trioxane 9b.

TABLE 3

| Dye | Temperature | Solvent | Acid catalyst | Reaction time | Yield |
|---|---|---|---|---|---|
| Tetraphenyl-Porphine | −10° C. | $CH_2Cl_2$ | HCl | 18 h | 52.9% |
| Rose Bengal | r.t. | EtOH* | Amberlyst-15 | 18 h | 56.8% |

*EtOH was removed under reduced pressure after photooxygenation and replaced by $CH_2Cl_2$ in the second step before the addition of 2-Adamantanone.

EXAMPLE 11

Trioxane 7be, Formula 7, R=Cyclohexyl, $R_1R_2$=—$CH_2$—$CH_2$—$CH(Ph)CH_2CH_2$—

A solution of 3-(4'-cyclohexylphenyl)-2-butenol (4b, 500 mg) and methylene blue (5 mg) in $CH_3CN$ (30 ml) was photooxygenated at −10° C. for 2.5 h. 4-Phenylcyclohexanone (1 g) and p-toluenesulfonic acid (50 mg) were added and the reaction mixture was left at r.t. for 20 h. The reaction mixture was worked up as above and concentrated. The crude product was purified by column chromatography on silica gel to furnish 570 mg (63.3% yield based on allylic alcohol 4b, used) of trioxane 7be as a mixture of two stereoisomers m.p. 107–109° C.

EXAMPLE 12

Ethyl 3-Hydroxy-3-(4'-Cycloheptylphenyl)-Butanoate (Compound 2c, Formula 2, R= Cycloheptyl)

To a refluxing mixture of 4'-cycloheptylacetophenone (25 g), $I_2$ (5 mg) and Zn (15 g) in benzene (200 ml) was added ethylbromoacetate (15 ml) dropwise during 1 h. The mixture was refluxed for 4.5 h and then cooled to room temperature. It was acidified with 10% HCl (200 ml) and benzene layer separated out. The organic layer was washed with water, dried ($Na_2SO_4$) and concentrated. The crude product was purified by column chromatography on silica gel to give 30.9 g (87.8% yield) of ethyl 3'-hydroxy-3-(4-cycloheptylphenyl)-butanoate (2c formula 2, R=cycloheptyl) as viscous oil.

Ethyl 3-(4'-Cycloheptylphenyl)-But-2-Enoate (Compound 3c, Formula 3, R=Cycloheptyl)

To a solution of ethyl 3-hydroxy-3-(4'-cycloheptylphenyl)-butanoate (2c, 28.75 g) in benzene (175 ml) was added p-toluenesulfonic acid and was refluxed for 1 h. The reaction mixture was diluted with NaHCO$_3$ and benzene layer was separated out. The organic layer was washed with water, dried (Na$_2$SO$_4$) and concentrated. The crude product was purified by column chromatography on silica gel to give 11.6 g (42.9% yield) of ethyl 3-(4'-cycloheptylphenyl)-but-2-enoate (3c, formula 3, R=cycloheptyl) as viscous oil.

3-(4'-Cycloheptylphenyl)-2-Butenol (Compound 4c, Formula 4, R=Cycloheptyl)

To an ice cooled slurry of LiAlH$_4$ (2.7 g) in dry ether (175 ml) was added a solution of ethyl 3-(4'-cycloheptylphenyl)-but-2-enoate (3c, 9.5 g) in dry ether (50 ml) dropwise. The mixture was stirred for 4 h. at 0° C. The reaction mixture was quenched with water (7 ml). A solution of 10% NaOH (3 ml) was added. The precipitate was washed with ether and combined ether extract was dried (Na$_2$SO$_4$) and concentrated. Crude product was purified by column chromatography on silica gel to give 6.1 g (75.3% yield) of allylic alcohol (4c, formula 4, R=cycloheptyl) as oil.

3-(4'-Cycloheptylphenyl)-1-Hydroxy-But-3-En-2-Hydroperoxide (Compound 5c, Formula 5, R=Cycloheptyl)

A solution of 3-(4'-cycloheptylphenyl)-2-butenol (4c, 150 mg) and methylene blue (2 mg) in acetonitrile (10 ml) was irradiated with a 250-watt tungsten-halogen lamp at −6° C. while oxygen was passed through the reaction mixture for 2.5 h. The reaction mixture was concentrated and crude product was purified by column chromatography on silica gel to furnish 120 mg (75% yield) of hydroperoxide 5c, m.p. 106–108° C.

3-[(4'-Cycloheptylphenyl)Vinyl]-1,2,5-Trioxaspiro-[5,5]-Undecane (Trioxane 7ca, Formula 7, R=Cycloheptyl; R$_1$R$_2$=—CH$_2$CH$_2$CH$_2$CH$_2$CH$_2$—)

A solution of 3-(4'-cycloheptylphenyl)-2-butenol (4c, 1 g) and methylene blue (5 mg) in CH$_3$CN (50 ml) was photooxygenated at −10° C. for 3 h. Cyclohexanone (3 ml) and p-toluenesulfonic acid (50 mg) were added and reaction mixture was stirred for 18 h at r.t. The reaction, mixture was worked up as above and concentrated. Crude product was purified by chromatography on silica gel to give 700 mg (50% yield, based on allylic alcohol, 4c used) of trioxane 7ca m.p. 55–57° C.

EXAMPLE 13

Trioxane 8c, Formula 8, R=Cycloheptyl

A solution of 3-(4'-cycloheptylphenyl)-2-butenol (4c, 500 mg) and methylene blue (5 mg) in CH$_3$CN (30 ml) was photooxygenated at −6° C. for 3.5 h. Norcamphor (500 mg) and p-toluenesulfonic acid (30 mg) were added and reaction mixture was stirred for 18 h. at r.t. The reaction mixture was worked up as above and concentrated. Crude product was purified by chromatotron on silica gel to furnish 290 mg (38.6% yield, based on allylic alcohol, 4c used) of trioxane 8c m.p. 65–68° C.

EXAMPLE 14

Trioxane 9c, Formula 9, R=Cycloheptyl

A solution of 3-(4'-cycloheptylphenyl)-2-butenol (4c, 500 mg) and methylene blue (5 mg) in CH$_3$CN (30 ml) was photooxygenated at −6° C. for 2 h. 2-Adamantanone (600 mg) and p-toluenesulfonic acid (50 mg) were added and reaction mixture was stirred for 22 h. at r.t. The reaction mixture was worked up as above and concentrated. Crude product was purified by chromatotron on silica gel to furnish 420 mg (50.6% yield, based on allylic alcohol, 4c used) of trioxane 9c as oil.

EXAMPLE 15

Trioxane 7cb, Formula 7, R=Cycloheptyl; R$_1$R$_2$=—CH$_2$—CH$_2$—CH[C(CH$_3$)$_2$CH$_2$CH$_3$]—CH$_2$CH$_2$—

A solution of 3-(4'-cycloheptylphenyl)-2-butenol (4c, 500 mg) and methylene blue (5 mg) in CH$_3$CN (30 ml) was photooxygenated at −6° C. for 3 h. 4-t-Amylcyclohexanone (1.5 ml) and p-toluenesulfonic acid (50 mg) were added and reaction mixture was stirred for 18 h. at r.t. The reaction mixture was worked up as above and concentrated. Crude product was purified by chromatotron on silica gel to furnish 400 mg (45.9% yield, based on allylic alcohol, 4c, used) of trioxane 7cb m.p. 58–60° C.

EXAMPLE 16

Ethyl 3-Hydroxy-3-(4'-Cyclooctylphenyl)-Butanoate (Compound 2d, Formula 2, R=Cyclooctyl)

To a refluxing mixture of 4'-cyclooctylacetophenone (30 g), I$_2$ (5 mg) and Zn (17.2 g) in benzene (300 ml) was added ethylbromoacetate (18 ml) dropwise during 30 minutes. The mixture was refluxed for 2 h and then cooled to room temperature. It was acidified with 10% HCl (200 ml), benzene layer was separated out. The organic layer was washed with water, dried (Na$_2$SO$_4$) and concentrated. The crude product was purified by column chromatography on silica gel to give 39.4 g (95% yield) of ethyl 3-hydroxy-3-(4'-cyclooctylphenyl)-butanoate (2d, formula 2, R=cyclooctyl) as viscous oil.

Ethyl 3-(4'-Cyclooctylphenyl)-But-2-Enoate (Compound 3d, Formula 3, R=Cyclooctyl)

To a solution of ethyl 3-hydroxy-3-(4'-cyclooctylphenyl)-butanoate (2d, 36 g) in benzene (350 ml) was added p-toluenesulfonic acid and refluxed for 2.5 h. The mixture was diluted with saturated NaHCO$_3$ solution (20 ml) and water (50 ml) and benzene layer was separated out. Aqueous layer was extracted with benzene (2×200 ml) combined organic layer was washed with water (2×20 ml), dried over Na$_2$SO$_4$ and concentrated. Crude product was purified by column chromatography to furnish 27.5 g (81.1% yield) of ethyl 3-(4'-cyclooctylphenyl)-but-2-enoate (3d, formula 3, R=cyclooctyl) as oil.

3-(4'-Cyclooctylphenyl)-2-Butenol (Compound 4d, Formula 4, R=Cyclooctyl)

To an ice cooled slurry of LiAlH$_4$ (2.9 g) in dry ether (200 ml) was added a solution of ethyl 3-(4'-cyclooctylphenyl)-but-2-enoate (3d, 10 g) in dry ether (50 ml) dropwise. The reaction mixture was stirred at 0° C. for 2 h. The reaction mixture was quenched with water (11 ml). A solution of 10% NaOH (10 ml) was added and ether layer was decanted. The precipitate was washed with ether and combined extracts were concentrated. The crude product was purified by column chromatography on silica gel to give 6.82 g (79.3% yield) of 3-(4'-cyclooctylphenyl)-2-butenol (4d, formula 4, R=cyclooctyl) m.p. 40–44° C.

3-(4'-Cyclooctylphenyl)-1-Hydroxy-But-3-En-2-Hydroperoxide (Compound 5d, Formula 5, R=Cyclooctyl)

A solution of 3-(4'-cyclooctylphenyl)-2-butenol (4d, 500 mg) and methylene blue (5 mg) in CH$_3$CN (30 ml) was irradiation with a 250-watt tungsten-halogen lamp at −6° C. while oxygen was passed through the reaction mixture. After 2.5 h the reaction mixture was concentrated and crude product was purified by column chromatography on silica gel to furnished 400 mg (71.4% yield), m.p.83–85° C.

3-Ethyl-3-Methyl-6-[(4'-Cyclooctylphenyl)Vinyl]-1,2,4-Trioxane (Compound 7da, Formula 7, R=Cyclooctyl)

A solution of 3-(4'-cyclooctylphenyl)-2-butenol (4d, 500 mg) and methylene blue (5 mg) in $CH_3CN$ (30 ml) was photooxygenated at −6° C. for 3 h. Ethyl methyl ketone (1 ml) and HCl (1 drop) were added and the reaction mixture was left at r.t. for 18 h. The reaction mixture was concentrated to remove $CH_3CN$, diluted with $NaHCO_3$ and water and extracted with ether (3×30 ml). The organic layer was dried over $Na_2SO_4$ and concentrated. The crude product was purified by chromatotron over silica gel to give 190 mg (28.7% yield based on allylic alcohol, 4d, used) of trioxane 7da as oil.

EXAMPLE 17

3-[(4'-Cyclooctylphenyl)Vinyl]-1,2,5-Trioxaspiro-(5,5)-Undecane (Trioxane 7db, Formula 7, R=Cyclooctyl; $R_1R_2$=—$CH_2CH_2CH_2CH_2CH_2$—)

A solution of 3-(4'-cyclooctylphenyl)-2-butenol (4d, 500 mg) and methylene blue (5 mg) in $CH_3CN$ (30 ml) was photooxygenated at −6° C. for 2.5 h. Cyclohexanone (1.5 ml) and p-toluenesulfonic acid (50 mg) were added and reaction mixture was left at r.t. for 18 h. The reaction mixture was worked up as above and concentrated. The crude product was purified by chromatron on silica gel to give 340 mg (47.8% yield, based on allylic alcohol, 4d used) of trioxane 7db as solid m.p. 58–60° C.

EXAMPLE 18

3-[(4'-Cyclooctylphenyl)Vinyl]-1,2,5-Trioxaspiro-(6,5)-Dodecane (Trioxane 7dc, R=Cyclooctyl; $R_1R_2$=—$CH_2CH_2CH_2CH_2CH_2CH_2$—)

A solution of 3-(4'-cyclooctylphenyl)-2-butenol (4d, 500 mg) and methylene blue (5 mg) in $CH_3CN$ (30 ml) was photooxygenated at −6° C. for 2.5 h. Cycloheptanone (1.5 ml) and p-toluenesulfonic acid (50 mg) were added and reaction mixture was left at r.t. for 18 h. The reaction mixture was worked up as above and concentrated. The crude product was purified by chromatotron on silica gel to furnish 210 mg (28.3% yield, based on allylic alcohol, 4d used) of trioxane 7dc as oil.

EXAMPLE 19

Trioxane 7dd, Formula 7, R=Cyclooctyl; $R_1R_2$=—$CH_2CH_2CH(Ph)CH_2CH_2$—)

A solution of 3-(4'-cyclooctylphenyl)-2-butenol (4d, 500 mg) and methylene blue (5 mg) in $CH_3CN$ (30 ml) was photooxygenated at −8° C. for 2.5 h. 4-Phenylcyclohexanone (1 g) and p-toluenesulfonic acid (50 mg) were added and reaction mixture was left at r.t. for 18 h. The reaction mixture was worked up as above and concentrated. The crude product was purified by chromatotron on silica gel to furnish 340 mg (39.5% yield, based on allylic alcohol, 4d used) of trioxane. 7dd as solid m.p. 95–97° C.

EXAMPLE 20

Trioxane 8d, Formula 8, R=Cyclooctyl

A solution of 3-(4'-cyclooctylphenyl)-2-butenol (4d, 500 mg) and methylene blue (5 mg) in $CH_3CN$ (30 ml) was photooxygenated at −6° C. for 2.5 h. Norcamphor (500 mg) and p-toluenesulfonic acid (50 mg) were added and reaction mixture was kept at 10° C. for 48 h. Reaction mixture was worked up as above and concentrated. Crude product was purified by chromatotron on silica gel to furnish 350 mg (47.5% yield, based on allylic alcohol 4d, used) of trioxane 8d as oil.

EXAMPLE 21

Trioxane 9d, Formula 9, R=Cyclooctyl

A solution of 3-(4'-cyclooctylphenyl)-2-butenol (4d, 500 mg) and methylene blue (5 mg) in $CH_3CN$ (30 ml) was photooxygenated at −10° C. for 3 h. 2-Adamantanone (500 mg) and p-toluenesulfonic acid (80 mg) were added and reaction mixture was stirred at r.t. for 4 h and then left at r.t. for 14 h. Reaction mixture was worked up as above and concentrated. Crude product was purified by chromatotron on silica gel to furnish 360 mg (44.4% yield, based on allylic alcohol 4d, used) of trioxane 9d as oil.

EXAMPLE 22

Ethyl 3-Hydroxy-3-([1,1'-Biphenyl]-4YL)-Butanoate (Compound 2e, Formula 2, R=Ph)

To a refluxing mixture of 4-acetylbiphenyl (20 g), $I_2$ (5 mg) and Zn (6.8 g) in benzene (200 ml) was added ethylbromoacetate (12 ml) dropwise during 30 minutes. The mixture was refluxed for 1 h and then cooled to room temperature. It was acidified with 10% HCl (100 ml) and benzene layer was separated out. The organic layer was washed with water, dried ($Na_2SO_4$) and concentrated. The crude product was purified by column chromatography on silica gel to give 20.6 g (72.1% yield) of ethyl 3-hydroxy-3-([1,1'-biphenyl]-4yl)butanoate (2e, formula 2, R=Ph) m.p. 58–60° C.

The above compound was also prepared using different reaction condition. Table 4 gives the condition used and yield of compound 2e.

TABLE 4

| Solvent | Temperature | Reaction time | Yield |
| --- | --- | --- | --- |
| Diethyl ether | r.t. | No reaction | — |
| Diethyl ether | Refluxed | No reaction | — |
| Toluene | Refluxed | 1 h | 92.8% |

The compound 2e was also prepared using ethylchloroacetate under same reaction conditions to furnish 17.8% yield of ethyl 3-hydroxy-3-([1,1'-biphenyl]-4yl)butanoate (2e).

Ethyl 3-([1,1'-Biphenyl]-4YL)-But-2-Enoate (Compound 3e, Formula 3, R=Ph)

To a solution of ethyl 3-hydroxy-3-([1,1'-biphenyl]-4yl)-butanoate (2e, 11 g) in benzene (250 ml) was added phosphorus pentoxide (4 g) and refluxed for 3 h. The benzene layer was decanted and then concentrated. The crude product was purified by column chromatography on silica gel to furnish 11 g (57.3% yield) of ethyl 3-([1,1'-biphenyl]-4yl)-but-2-enoate (3e, formula 3, R=Ph) m.p. 76–78° C.

The compound 3e was also prepared using different reaction condition. Table 5 gives the conditions used and the yield of compound 3e.

TABLE 5

| Acid catalyst | Solvent | Temperature | Reaction time | Yield (%) |
|---|---|---|---|---|
| PTSA | Benzene | Refluxed | 1 h | 55.5 |
| Amberlyst-15 | Toluene | Refluxed | 1 h | 77.7 |
| $I_2$ | Benzene | Refluxed | 1 h | 88.8 |
| $H_2SO_4$ | $CHCl_3$ | r.t. | 18 h | 33.3 |

3-([1,1'-Biphenyl]-4YL)-2-Butenol (Compound 4e, Formula 4, R=Ph)

To an ice cooled slurry of $LiAlH_4$ (4.0 g) in dry ether (400 ml) was added ethyl 3-([1,1'-biphenyl]-but-2-enoate (3e, 11 g) in dry ether (200 ml) dropwise. The mixture was stirred at 0° C. for 2 h. The reaction mixture was quenched with water (10 ml). A solution of 10% NaOH (5 ml) was added, stirred and then ether layer was decanted. The precipitate was washed with ether and combined ether extracts were concentrated. The crude product was purified by chromatography on silica gel to give 7.2 g (77.4% yield) of 3-([1,1'-biphenyl]-4yl)-2-butenol (4e formula 4, R=Ph), m.p. 112–114° C.

$LiAlH_4$ reduction of ethyl 3-([1,1'-biphenyl]-but-2-enoate (3e) using THF as solvent under similar conditions furnished 40.6% yield of 3-([1,1'-biphenyl]-4yl)-2-butenol (4e).

3-([1,1'-Biphenyl]-4YL)-1-Hydroxy-But-3-En-2-Hydroperoxide (Compound 5e, Formula 5, R=Ph)

A solution of 3-([1,1-biphenyl]-4yl)-2-butenol (4e, 200 mg) and methylene blue (2 mg) in acetonitrile (15 ml) was irradiated with 250-watt tungsten-halogen lamp at −6° C. while oxygen was passed through the reaction mixture. After 4 h the reaction mixture was concentrated. The reaction mixture was filtered through a cintered crucible to furnish 80 mg of hydroperoxide. Mother liquor was purified by column chromatography to furnish 40 mg of hydroperoxide. The combined yield of hydroperoxide (compound 5e, formula 5, R=Ph) was 120 mg (54.5% yield) m.p. 124° C.

Phototoxygenation of 3-([1,1'-biphenyl]-4yl)-2-butenol (4e), in $CHCl_3$ at 0° C., using tetraphenylporphine as sensetizer furnished 5e in 81.8% yield.

6-[([1,1'-Biphenyl]-4YL)Vinyl]-3-Phenyl-1,2,4-Trioxane (Trioxane 7ea, Formula 7, R=Ph, $R_1$, $R_2$= H, Ph).

To a solution of 3-([1,1'-biphenyl]-4yl)-1-hydroxy-but-3-en-2-hydroperoxide (5e, 400 mg) and benzaldehyde (350 mg) in acetonitrile (10 ml) was added p-toluenesulfonic acid (20 mg) and was stirred at r.t. for 2 h. The reaction mixture was worked up as above and concentrated. Crude product was purified by column chromatography to furnish 280 mg (70% yield) of trioxane 7ea m.p. 110–112° C.

EXAMPLE 23

8-[([1,1'-Biphenyl]-4YL)Vinyl]-6,7,10-Trioxaspiro(4,5)Decane (Trioxane 7eb, Formula 7, R=Ph, $R_1R_2$=—$CH_2CH_2CH_2CH_2$—)

To a solution of 3-([1,1'-biphenyl]-4yl)-1-hydroxy-but-3-en-hydroperoxide (5e, 430 mg) and cyclopentanone (700 mg) in acetonitrile (10 ml) was added p-toluenesulfonic acid (30 mg) and the reaction mixture was stirred at r.t. for 3 h. The reaction mixture was worked up as above and concentrated. The crude product was purified by column chromatography followed by crystallization from hexane to furnish 250 mg (45.1% yield) of trioxane 7eb, m.p. 102–104° C.

EXAMPLE 24

3-[([1,1'-Biphenyl]-4YL)Vinyl]-1,2,5-Trioxaspiro(5,5)Undecane (Trioxane 7ec, Formula 7, R=Ph, $R_1R_2$=—$CH_2CH_2CH_2CH_2CH_2$—)

To a solution of 3-([1,1-biphenyl]-4yl)-1-hydroxy-but-3-en-2-hydroperoxide (5e, 600 mg) and cyclohexanone (1 ml) in acetonitrile (20 ml) was added p-toluenesulfonic acid (20 mg) and the reaction mixture was stirred at r.t. for 1 h. The reaction mixture was worked up as above and concentrated. The crude product was purified by column chromatography followed by crystallization from hexane to furnish 360 mg (46.1% yield) of trioxane 7ec, m.p. 96–98° C.

EXAMPLE 25

3-Decyl-3-Methyl-6-[([1,1'-Biphenyl]-4-YL)-Vinyl]-1,2,4-Trioxane (Trioxane 7ed, Formula 7, R=Ph; $R_1$, $R_2$=$CH_3$, —$CH_2(CH_2)_8CH_3$)

A solution of 3-([1,1'-biphenyl]-4yl)-2-butenol (4e, 200 mg) and methylene blue (2 mg) in acetonitrile (10 ml) and chloroform (10 ml) was photooxygenated at 0° C. for 3 h. 2-dodecanone (0.5 ml) and hydrochloric acid (2 drops) were added and reaction mixture of left at r.t. for 18 h. The reaction mixture was worked up and concentrated. Crude product was purified by column chromatography on silica gel to furnish 100 mg mg (27% yield, based on allylic alcohol, 4e, used) of trioxane 7ed m.p. 86–90° C.

EXAMPLE 26

Trioxane 8e, Formula 8, R=Ph

A solution of 3-([1,1'-biphenyl]-4yl)-2-butenol (4e, 200 mg) and methylene blue (2 mg) in acetonitrile (15 ml) was photooxygenated at −10° C. for 3 h. Norcamphor (250 mg) and p-toluene sulfonic acid (30 mg) were added and reaction mixture was left at r.t. for 18 h. The reaction mixture was worked up and concentrated. Crude product was purified by column chromatography on silica gel to furnish 140 mg (45.1% yield, based on allylic alcohol, 4e, used) of trioxane 8e m.p. 86–90° C.

EXAMPLE 27

Trioxane 9e, Formula 9, R=Ph

To a solution of 3-([1,1'-biphenyl]-4yl)-1-hydroxy-but-3-en-2-hydroperoxide (5e, 300 mg) and 2-Adamantanone (250 mg) in acetonitrile (20 ml) was added p-toluenesulfonic acid (30 mg) and was stirred for 1 h at r.t. The reaction mixture was worked up and concentrated. Crude product was purified by column chromatography on silica gel to furnish 320 mg (71.04% yield) of trioxane 9e, m.p. 94–96° C.

The above trioxane was also prepared from 4e using different reaction conditions. Table 6 gives the conditions used and the yields of the trioxane 9e.

TABLE 6

| Dye | Temperature | Solvent | Acid catalyst | Reaction time | Yield[a] |
|---|---|---|---|---|---|
| Tetraphenyl-Porphine | r.t. | $CHCl_3$ | $H_2SO_4$ | 30 min | 55.5% |
| Rose Bengal | −6° C. | EtOH* | Amberlyst-15 | 2 h | 24.4% |

*EtOH was removed under reduced pressure after photooxygenation and replaced by $CHCl_3$ in the second step before the addition of 2-Adamantanone.
[a]Yields based on allylic alcohols 4e used.

EXAMPLE 28

Ethyl 3-Hydroxy-3-(4'-Bromo[1,1'-Biphenyl]-4-YL)-Butanoate (Compound 2f, Formula 2, R=p-Br—$C_6H_4$)

To a refluxing mixture of 4-(4-bromophenyl) acetophenone (10 g), $I_2$ (5 mg) and Zn (4.9 g) in benzene (100 ml) was added ethylbromoacetate (6.1 ml) dropwise during 45 minutes. The mixture was refluxed for 45 minutes and then cooled to room temperature. It was acidified with 10% HCl (75 ml) and benzene layer was separated. Organic layer was washed with water, dried ($Na_2SO_4$) and concentrated. Crude product was crystallized from hexane to furnish 8 g of β-hydroxyester (2f). Mother liquor was purified by column chromatography on silica gel to furnish 3.7 g of β-hydroxyester (2f). The combined yield of β-hydroxyester (compound 2f, formula 2, R=p-Br—$C_6H_4$) was 11.7 g (88.9%), m.p. 70° C.

Ethyl 3-(4'-Bromo-[1,1'-Biphenyl]-4-YL)-But-2-Enoate (Compound 3f, Formula 3, R=p-Br—$C_6H_4$)

To a solution of ethyl 3-hydroxy-3-(4'-bromo[1,1'-biphenyl]-4-yl)-butanoate (2f, 8.0 g) in benzene (75 ml) was added p-toluenesulfonic acid (420 mg) and was refluxed for 1 h 15 minutes. The reaction mixture was cooled, neutralized with $NaHCO_3$ solution, diluted with water and organic layer was extracted. Organic layer was washed with water, dried ($Na_2SO_4$) and concentrated. Crude product was purified by column chromatography on silica gel to furnish 5 g (65.7% yield) of ethyl 3-hydroxy-3-(4'-bromo[1,1'-biphenyl]-4-yl)-but-2-enoate (3f, formula 3, R=p-Br—$C_6H_4$) m.p. 96–98° C.

3-(4'-Bromo-[1,1'-Biphenyl]-4-YL)-2-Butenol (Compound 4f, Formula 4, R=p-Br—$C_6H_4$)

To an ice cooled slurry of $LiAlH_4$ (2.0 g) in dry ether (200 ml) was added a solution of ethyl 3-hydroxy-3-(4'-bromo-[1,1'-biphenyl]-4-yl)-but-2-enoate (3f, 4.4 g) in dry ether (100 ml) dropwise. The reaction mixture was stirred for 5 h at 0° C. The reaction mixture was quenched with water (5 ml). A solution of 10% NaOH (5 ml) was added and the ether layer was decanted. The precipitate was washed with ether and the combined ether extract was concentrated. The crude product was chromatographed on silica gel to give 2 g (52.6% yield) of 3-(4'-bromo-[1,1'-biphenyl]-4-yl)-2-butenol (4f, formula 4, R=p-Br—$C_6H_4$) m.p. 145–148° C.

3-(4'-Bromo-[1,1'-Biphenyl]-4YL)-1-Hydroxy-But-3-En-2-Hydroperoxide (Compound 5f, Formula 5, R=p-Br—$C_6H_4$)

A solution of 3-(4'-bromo-[1,1'-biphenyl]-4-yl)-2-butenol (4f, 100 mg) and methylene blue (5 mg) in acetonitrile (7 ml) and $CH_2Cl_2$ (7 ml) was irradiated with a 250 watt tungsten-halogen lamp at −6° C. while oxygen was passed through the reaction mixture for 5 h. The crude product obtained by usual aqueous workup was crystallized from $CH_2Cl_2$ to give 20 mg of hydroperoxide 5f. The filtrate was chromatographed on silica gel to give 40 mg of hydroperoxide 5f. The combined yield of hydroperoxide (compound 5f, formula 5, R=p-Br—$C_6H_4$) was 60 mg (55% yield).

3,3-Dimethyl-6-[(4'-Bromo-[1,1'-Biphenyl]-4-YL)-Vinyl]-1,2,4-Trioxane (Trioxane 7fa, Formula 7, R= p-Br—$C_6H_4$; $R_1$, $R_2$=$CH_3$, $CH_3$)

A solution of 3-(4'-bromo-[1,1'-biphenyl]-4-yl)-2-butenol (4f, 350 mg) and methylene blue (2 mg) in acetone (40 ml) was photooxygenated at −10° C. for 5 h. To the mixture was added p-toluenesulfonic acid (50 mg) and left at r.t. for 18 h and then concentrated. The crude product was purified by column chromatography to give 300 mg (69.7% yield) of trioxane 7fa m.p. 92–95° C.

EXAMPLE 29

3-Ethyl-3-Methly-6-[(4'-Bromo-[1,1'-Biphenyl]-4-YL)-Vinyl]-1,2,4-Trioxane (Trioxane 7fb, Formula 7, R=p-Br—$C_6H_4$; $R_1$, $R_2$=$CH_3$, $CH_2CH_3$)

A solution of 3-(4'-bromo-[1,1'-biphenyl]-4-yl)-2-butenol (4f, 500 mg) and methylene blue (5 mg) in $CH_3CN$ (40 ml) and $CH_2Cl_2$ was photooxygenated at −6° C. for 3 h. To the mixture was added ethyl methyl ketone (3 ml) and p-toluenesulfonic acid (40 mg) and left at r.t. for 18 h. The reaction mixture was diluted with saturated $NaHCO_3$ solution (5 ml) and worked up as above and concentrated. The crude product was purified by column chromatography to give 240 mg (37.5% yield) of trioxane 7fb as a mixture of two stereoisomers, which were further, purified to furnish the more polar isomer, m.p. 72–74° C. and less polar isomer, m.p. 82–85° C.

EXAMPLE 30

3-[(4'-Bromo-[1,1'-Biphenyl]-4-YL)-Vinyl]-1,2,5-Trioxaspiro(5,5)Undecane (Trioxane 7fc, Formula 7, R=p-Br—$C_6H_4$; $R_1R_2$=$CH_2CH_2CH_2CH_2CH_2$—)

A solution of 3-(4'-bromo-[1,1'-biphenyl]-4-yl)-2-butenol (4f, 500 mg) and methylene blue (5 mg) in $CH_3CN$ (35 ml) and $CH_2Cl_2$ (35 ml) was photooxygenated at −6° C. for 3.5 h. Cyclohexanone (1 ml) and p-toluenesulfonic acid (60 mg) were added and reaction mixture was left at r.t. for 18 h. The reaction mixture was diluted with saturated $NaHCO_3$ solution (5 ml) and worked up as above and concentrated. Crude product was purified by column chromatography to furnish 320 mg (47% yield, based on allylic alcohol 4f, used) of trioxane 7fc, m.p. 118–120° C.

EXAMPLE 31

Trioxane 7fd, Formula 7, R=p-Br—$C_6H_4$, $R_1R_2$==—$CH_2CH_2$—$CH[C(CH_3)_2CH_2CH_3]$—$CH_2CH_2$-

A solution of 3(4'bromo-[1,1'biphenyl]-4yl)-2-butenol (4f, 500 gm) and methylene blue (2 mg) in $CH_3CN$ (40 ml) and $CH_2Cl_2$ (40 ml) was photooxygenated at −6° C. for 3 h. 4-t-amyl cyclohexanone (1.5 ml) and p-toluenesulfonic acid (50 mg) were added and reaction mixture was left at r.t. for 17 h. The reaction mixture was worked up and concentrated. Crude product was purified by column chromatography to furnish 480 mg (60% yield, based on allylic alcohol, 4f used) of trioxane 7fd m.p. 122–124° C.

EXAMPLE 32

Trioxane 8f, Formula 8, R=p-Br—$C_6H_4$

A solution of 3(4'-bromo-[1,1'-biphenyl]-4yl)-2-butenol (4f, 350 mg) and methylene blue (2 mg) in $CH_3CN$ (25 ml) and $CH_2Cl_2$ (25 ml) was photooxygenated at −6° C. for 3 h. Norcamphor (750 mg) and p-toluenesulfonic acid (50 mg) were added and the reaction mixture was stirred at r.t. for 18 h. The reaction mixture was worked up as above and concentrated. Crude product was purified by column chromatography on silica gel to furnish 300 mg (42.8% yield, based on allylic alcohol, 4f used) of trioxane 8f, m.p. 122–124° C.

EXAMPLE 33

Trioxane 9f, Formula 9, R=p-Br—$C_6H_4$

A solution of 3-(4'-bromo-[1,1'-biphenyl]-4yl)-2-butenol (4f, 500 mg) and methylene blue (2 mg) in $CH_3CN$ (40 ml) and $CH_2Cl_2$ (40 ml) was photoooxygenated at 5° C. for 5 h. 2-Adamantanone (1 g) and p-toluenesulfonic acid (60 mg) were added and reaction mixture was stirred for 30 minutes and then left at r.t. for 16 h. Reaction mixture was worked as above and concentrated. Crude product was purified by column chromatography to furnish 490 mg (63.6% yield, based on allylic alcohol 4f, used) of trioxane 9f mp 118° C.

EXAMPLE 34

Ethyl 3-(4'-Chloro-[1,1'-Biphenyl]-4-YL)-But-2-Enoate (Compound 3g, Formula 3, R=p-Cl—$C_6H_4$)

To a refluxing mixture of 4-(4-chlorophenyl) acetophenone (8.46 g), $I_2$ (5 mg) and Zn (2.55 g) in benzene (200 ml) was added ethylbromoacetate (4.35 ml) dropwise during 30 minutes. The mixture was refluxed for 2 h and then cooled to room temperature. It was acidified with 10% HCl (75 ml) and benzene layer was separated. Organic layer was washed with water, dried ($Na_2SO_4$) and concentrated. Crude β-hydroxyester (compound 2g, formula 2, R=p-Cl—$C_6H_4$) was used as such without purification for the preparation of ethyl 3-(4'-chloro-[1,1'-biphenyl]-4-yl)-but-2-enoate as follows:

To a solution of crude ethyl 3-hydroxy-3-(4'-chloro-[1,1'-biphenyl]-4-yl)-butanoate (2g) in benzene (200 ml) was added p-toluenesulfonic acid (3 gm) and was refluxed for 3 h 30 minutes. The reaction mixture was cooled, neutralized with $NaHCO_3$ solution, diluted with water and organic layer was extracted. Organic layer was washed with water, dried ($NaHCO_3$) and concentrated. Crude product was purified by column chromatography on silica gel to furnish 5.27 g (47.=91% yield) of ethyl 3-(4'-chloro-[1,1'-biphenyl]-4-yl)-but-2-enoate (3g, formula 3, R=p-Cl—$C_6H_4$) m.p. 91–94° C.

3-(4'-Chloro-[1,1'-Biphenyl]-4-YL)-2-Butenol (Compound 4g, Formula 4, R=p-Cl—$C_6H_4$)

To an ice cooled slurry of $LiAlH_4$ (1.4 g) in dry ether (200 ml) was added a solution of ethyl 3-(4'-chloro-[1,1'-biphenyl]-4-yl)-but-2-enoate (3g, 2.8 g) in dry ether (50 ml) dropwise. The reaction mixture was stirred for 2 h at 0° C. The reaction mixture was quenched with water. A solution of 10% NaOH was added and the ether layer was decanted. The precipitate was washed with ether and the combined ether extract was concentrated. The crude product was chromatographed on silica gel to give 1.8 g (75% yield) of 3-(4'-chloro-[1,1'-biphenyl]-4-yl)-butenol (4g, formula 4, R=p-Cl—$C_6H_4$) m.p. 130–132° C.

3-(4'-Chloro-[1,1'-Biphenyl]-4YL)-1-Hydroxy-But-3-En-2-Hydroperoxide (Compound 5g, Formula 5, R=p-Cl—$C_6H_4$)

A solution of 3-(4'-chloro-[1,1'-biphenyl]-4-yl)-2-butenol (4g, 1 g) and methylene blue (40 mg) in acetonitrile (30 ml) was irradiation with a 250-watt tungsten-halogen lamp at 10° C. while oxygen was passed through the reaction mixture for 5 h 30 minutes. Solid hydroperoxide separated out during the reaction was collected by filtration to furnish 600 mg of hydroperoxide 5g. The filtrate was chromatographed on silica gel to give 260 mg of hydroperoxide 5g. The combined yield of hydroperoxide (compound 5g, formula 5, R=p-Cl—$C_6H_4$) was 860 mg (76.7% yield).

8-[(4'-Chloro-[1,1'-Biphenyl]-4YL)Vinyl]-6,7,10-Trioxaspiro(4,5)Decane (Trioxane 7ga, Formula 7, R=p-Cl—$C_6H_4$, $R_1R_2$=—$CH_2CH_2CH_2CH_2$—)

A solution of 3-(4'-chloro-[1,1'-biphenyl]4yl)-2-butenol (4g, 500 gm) and methylene blue (40 mg) in $CH_3CN$ (30 ml) was photooxygenated at 5° C. for 5 h. Cyclopentanone (0.5 ml) and hydrochloric acid (5 drops) were added and reaction mixture was stirred at r.t. for 1.5 h and then left at r.t for 48 h. The reaction mixture was concentrated. Crude product was purified by column chromatography to furnish 230 mg (33.8% yield, based on allylic alcohol, 4g used) of trioxane 7ga m.p. 105–107° C.

EXAMPLE 35

3-[(4'-Chloro-[1,1'-Biphenyl]-4-YL)-Vinyl]-1,2,5-Trioxaspiro(5,5)Undecane (Trioxane 7gb, Formula 7, R=p-Cl—$C_6H_4$; $R_1R_2$=$CH_2CH_2CH_2CH_2CH_2$—)

A solution of 3-[(4'-chloro-[1,1'-biphenyl]-4-yl)-2-butenol (4g, 500 mg) and methylene blue (40 mg) in $CH_3CN$ (30 ml) was photooxygenated at 5° C. for 5 h. Cyclohexanone (0.5 ml) and hydrochloric acid (5 drops) were added and reaction mixture was stirred at r.t. for 1.5 h and then left at r.t for 24 h. The reaction mixture was concentrated. Crude product was purified by column chromatography to furnish 360 mg (50% yield, based on allylic alcohol 4g, used) of trioxane 7gb, m.p. 109–111° C.

EXAMPLE 36

Trioxane 8g, Formula 8, R=p-Cl—$C_6H_4$

To a solution of 3-(4'-chloro-[1,1'-biphenyl]-4yl)-1-hydroxy-but-3-en-2-hydroperoxide (5g, 500 mg) and norcamphor (500 mg) in chloroform (100 ml) was added hydrochloric acid (5 drops) and the reaction mixture was stirred at r.t. for 1 h and then left at r.t for 18 h. The reaction mixture was worked up as above and concentrated. Crude product was purified by column chromatography on silica gel followed by crystallization to furnish 420 mg (64.6% yield) of trioxane 8g, m.p. 122–124° C.

EXAMPLE 37

Trioxane 9g, Formula 9, R=p-Cl—$C_6H_4$

A solution of 3-(4'-chloro-[1,1'-biphenyl]-4yl)-2-butenol (4g, 500 mg) and methylene blue (50 mg) in $CH_3CN$ (60 ml) was photoooxygenated at 5° C. for 5 h. 2-Adamantanone (1 g) and hydrochloric acid (5 drops) were added and reaction mixture was stirred at r.t. for 2 h and then left at r.t for 16 h. The reaction mixture was worked up and concentrated. Crude product was purified by column chromatography to furnish 560 mg (69.14% yield, based on allylic alcohol 4g, used) of trioxane 9g, m.p. 112–115° C.

Following the Above Procedure the Following Trioxanes Were Prepared

| S. No. | Trioxane | m.p. | % Yield |
|---|---|---|---|
| 1. | 8-[(4'-Cyclopentylphenyl)vinyl]-6,7,10-trioxaspiro-[4,5]-decane (trioxane 7aa, formula 7, R = cyclopentyl; $R_1 R_2$ = $-CH_2CH_2CH_2CH_2$) | oil | 52.7 |
| 2. | Trioxane 7ab, formula 7, R = cyclopentyl; $R_1 R_2$ = $-CH_2CH_2CH(Ph)CH_2CH_2-$ | 98–100° C. | 60.2 |
| 3. | 3-[(4'-cyclopentylphenyl)vinyl]-1,2,5-trioxaspiro(5,5)undecane (7ac, formula 7, R = cyclopentyl, $R_1 R_2$ = $-CH_2CH_2CH_2CH_2CH_2-$) | 57–58° C. | 50.6 |
| 4. | 3-[(4'-cyclopentylphenyl)vinyl-1,2,5-trioxaspira (5,6)dodecane (7ad, formula 7, R = cyclopentyl, $R_1R_2$ = $-CH_2CH_2CH_2CH_2CH_2CH_2-$) | Oil | 29.1 |
| 5. | Trioxane 7ae, formula 7, R = cyclopentyl, $R_1 R_2$ = $CH_2-CH_2-CH(C(CH_3)_2CH_2CH_3)-CH_2CH_2-$ | 95–97° C. | 47.8 |
| 6. | Trioxane belonging to norcamphor group (8a R = cyclopentyl) | 91–93° C. | 28 |
| 7. | Trioxane belonging to adamantane group (9a R = cyclopentyl) | 74–76° C. | 49.4 |
| 8. | 3,3-dimethyl-6-[4'-cyclohexylphenyl]vinyl-1,2,4-trioxane (trioxane 7ba, formula 7, R = cyclohexyl) | 54–55° C. | 76.9 |
| 9. | 3-Decyl-3-methyl-6-[(4'-cyclohexylphenyl)vinyl]-1,2,4-trioxane (trioxane 7bb, formula 7, R = cyclohexyl) | oil | 31.1 |
| 10 | 6-[(4'-cyclohexylphenyl)vinyl]-3-phenyl-1,2,4-trioxane (trioxane 7bc, formula 7, R = cyclohexyl] | 86–88 ° C. | 44.7 |
| 11 | 3-[(4'-Cyclohexylphenyl)vinyl]-1,2,5-trioxaspiro(5,5)undecane (trioxane 7bd, formula 7, R = cyclohexyl, $R_1R_2$ = $-CH_2CH_2CH_2CH_2CH_2-$) | 60–62° C. | 74.3 |
| 12. | Trioxane 7be, formula 7, R = cyclohexyl, $R_1 R_2$ = $-CH_2-CH_2-CH(Ph)CH_2CH_2-$ | 107–109° C. | 63.3 |
| 13. | 3-ethyl-3-methyl-6-[4'-cyclohexyl phenyl)vinyl]-1,2,4-trioxane (7bf, formula 7, R = cyclohexyl, $R_1$, $R_2$ = $CH_3$, $-CH_2CH_3$) | Oil | 20 |
| 14. | 3-Methyl-3-propyl-6-[4'-cyclohexyl phenyl)vinyl]-1,2,4-trioxane (7bg, formula 7, R = cyclohexyl, $R_1$, $R_2$ = $CH_3$, $-CH_2CH_2CH_3$) | Oil | 28.1 |
| 15. | 8-[(4'-cyclohexylphenyl)vinyl]-6,7,10-trioxaspiro (4,5) decane (7bh, formula 7, R = cyclohexyl, $R_1$ $R_2$ = $-CH_2-CH_2-CH_2-CH_2-$) | 43–45° C. | 39.4 |
| 16. | Trioxane 7bi, formula 7, R = cyclohexyl, $R_1$ $R_2$ = $CH_2-CH_2-CH(C(CH_3)_2CH_2CH_3)-CH_2CH_2-$ | 90–92° C. | 50.5 |
| 17. | Trioxane belonging to norcamphor group (8b R = cyclohexyl) | 70–71° C. | 40.8 |
| 18. | Trioxane belonging to adamantane group (9b R = cyclohexyl) | 75–76° C. | 58.8 |
| 19. | 3-(4'-cycloheptylphenyl)vinyl]-1,2,5-trioxaspiro-[5,5]-undecane (trioxane 7ca, formula 7, R = cycloheptyl; $R_1 R_2$ = $-CH_2CH_2CH_2CH_2CH_2-$) | 55–57° C. | 50 |
| 20. | Trioxane 7cb, formula 7, R = cycloheptyl; $R_1 R_2$ = $-CH_2-CH_2-CH(C(CH_3)_2CH_2CH_3)-CH_2CH_2-$ | 58–60° C. | 45.9 |
| 21. | 8-[(4'-cycloheptylphenyl)vinyl]-6,7,10-trioxaspiro(4,5)decane (7cc, formula 7, R = cycloheptyl, $R_1$ $R_2$ = $CH_2-CH_2-CH_2-CH_2-$ | Oil | 65 |
| 22. | Trioxane 7cd, formula 7, R = cycloheptyl, $R_1R_2$ = $CH_2-CH_2-CH(Ph)-CH_2-CH_2-$) | 92–95° C. | 44 |
| 23. | Trioxane belonging to norcamphor group (8c R = cycloheptyl) | 65–68° C. | 38.6 |
| 24. | Trioxane belonging to adamantane group (9c R = cycloheptyl) | oil | 50.6 |
| 25. | 3-ethyl-3-methyl-6-[(4'-cyclooctylphenyl) vinyl]-1,2,4-trioxane (compound 7da, formula 7, R = cyclooctyl) | oil | 28.7 |
| 26. | 3-[(4'-cyclooctylphenyl)vinyl]-1,2,5-trioxaspiro-(5,5)-undecane (trioxane 7db, formula 7, R = cyclooctyl; $R_1 R_2$ = $-CH_2CH_2CH_2CH_2CH_2-$) | 58–60° C. | 47.8 |
| 27. | 3-[(4'-cyclooctylphenyl)vinyl]-1,2,5-trioxaspiro-(6,5)-dodecane (trioxane 7dc, formula 7, R = cyclooctyl; $R_1 R_2$ = $-CH_2CH_2CH_2CH_2CH_2CH_2-$) | oil | 28.3 |
| 28. | Trioxane 7dd, formula 7, R = cyclooctyl, $R_1R_2$ = $CH_2-CH_2-CH(Ph)-CH_2-CH_2-$) | 95–97° C. | 39.5 |
| 29. | 8-[(4'-cyclooctylphenyl)vinyl]-6,7,10-trioxaspiro(4,5)undecane (7de, formula 7, R = cycloheptyl, $R_1R_2$ = $CH_2-CH_2-CH_2-CH_2-$) | Oil | 45.5 |
| 30. | Trioxane 7df, formula 7, R = cyclooctyl, $R_1R_2$ = $CH_2-CH_2-CH(C(CH_3)_2CH_2CH_3)-CH_2CH_2-$ | 89–91° C. | 51.7 |
| 31. | Trioxane belonging to norcamphor group (8d R = cyclooctyl) | oil | 47.5 |
| 32. | Trioxane belonging to adamantane group (9d R = cyclooctyl) | oil | 44.4 |
| 33. | 6-[([1,1'-biphenyl]-4yl)vinyl]-3-phenyl-1,2,4-trioxane (7ea, formula 7, R = Ph, $R_1,R_2$ = H, Ph). | 110–112°C. | 70 |
| 34. | 8-[([1,1'-biphenyl]-4yl)vinyl]-6,7,10-trioxaspiro (4,5) decane (7eb, formula 7, R = Ph, $R_1 R_2$ = $-CH_2CH_2CH_2CH_2-$) | 102–104° C. | 45.1 |
| 35. | 3-[([1,1'-biphenyl]-4yl)vinyl]-1,2,5-trioxaspiro (5,5) undecane (7ec, formula 7, R = Ph, $R_1R_2$ = $-CH_2CH_2CH_2CH_2CH_2-$) | 96–98° C. | 46.1 |
| 36. | 3-Decyl-3-Methyl-6-[([1,1'-biphenyl]-4-yl)-vinyl]-1,2,4-trioxane (7ed, formula 7, R = Ph; $R_1$, $R_2$ = $CH_3$, $-CH_2(C_2)_8CH_3$) | 86–90° C. | 27 |
| 37. | 3,3-Dimethyl-6-[([1,1'-biphenyl]-4yl)vinyl]-1,2,4-trioxane (7ee, formula 7, R = Ph, $R_1$, $R_2$ = $CH_3,CH_3$) | 90–92° C. | 37.2 |
| 38. | Trioxane 7ef, formula 7, R = Ph, $R_1 R_2$ = $-CH_2CH_2CH(Ph)CH_2CH_2-$ | 150–154° C. | 81 |
| 39. | Trioxane 7eg, formula 7, R = Ph, $R_1R_2$ = $CH_2-CH_2-CH(C(CH_3)_2CH_2CH_3)-CH_2CH_2-$) | 94–98° C. | 85.5 |
| 40. | 3[([1,1'-biphenyl]-4yl)vinyl]-1,2,5-trioxaspiro(5,6)dodecane (7eh, formula 7, R = Ph, $R_1$ $R_2$ = $CH_2CH_2CH_2CH_2CH_2 CH_2-$) | 90–92° C. | 24.6 |
| 41. | Trioxane belonging to norcamphor group (8e R = Ph) | 86–90° C. | 45.1 |
| 42. | Trioxane belonging to adamantane group (9e R = Ph) | 94–96° C. | 71.04 |
| 43. | 3,3-Dimethyl-6-[(4'-bromo-[1,1'-biphenyl]-4-yl)-vinyl]-1,2,4-trioxane (7fa, formula 7, R = p-Br-$C_6H_4$; $R_1$, $R_2$ = $CH_3$, $CH_3$) | 92–95° C. | 69.7 |

-continued

| S. No. | Trioxane | m.p. | % Yield |
|---|---|---|---|
| 44. | 3-Ethyl-3-methly-6-[(4'-bromo-[1,1'-biphenyl]-4-yl)-vinyl]-1,2,4-trioxane (7fb, formula 7, R = p-Br—$C_6H_4$; $R_1$, $R_2$ = $CH_3$, $CH_2CH_3$) | 82–85° C. | 37.5 |
| 45. | 3-[(4'-bromo-[1,1'-biphenyl]-4-yl)-vinyl]-1,2,5-trioxaspiro (5,5) undecane (7fc , formula 7, R = p-Br—$C_6H_4$; $R_1 R_2$ = $CH_2CH_2CH_2CH_2CH_2$—) | 118–120° C. | 47 |
| 46. | Trioxane 7fd, formula 7, R = p-Br—$C_6H_4$, $R_1 R_2$ == —$CH_2$—$CH_2$—CH[C($CH_3$)$_2$$CH_2CH_3$]— $CH_2$—$CH_2$— | 122–124° C. | 60 |
| 47. | 8-[(4'-bromo-[1,1'-biphenyl]-4yl)vinyl]-6,7,10-trioxaspiro (4,5) decane (7fe, formuma 7, R = p-Br—$C_6H_4$, $R_1 R_2$ = —$CH_2$—$CH_2$—$CH_2$—$CH_2$—) | 104–106° C. | 66.6 |
| 48. | Trioxane 7ff, formula 7, R = p-Br—$C_6H_4$, $R_1 R_2$ = $CH_2$—$CH_2$—CH(Ph)—$CH_2$—$CH_2$— | 104–106° C. | 66.6 |
| 49. | Trioxane belonging to norcamphor group (8f R = p-Br—$C_6H_4$) | 122–124° C. | 42.8 |
| 50. | Trioxane belonging to adamantane group (9f R = p-Br—$C_6H_4$) | 118° C. | 63.6 |
| 51. | 8-[(4'-chloro-[1,1'-biphenyl]-4yl)vinyl]-6,7,10-trioxaspiro (4,5) decane (7ga, formula 7, R = p-Cl—$C_6H_4$, $R_1R_2$ = —$CH_2CH_2CH_2CH_2$—) | 105–107° C. | 33.8 |
| 52 | 3-[(4'-chloro-[1,1'-biphenyl]-4-yl)-vinyl]-1,2,5-trioxaspiro (5,5) undecane (7gb, formula 7, R = p-Cl—$C_6H_4$; $R_1 R_2$ = $CH_2CH_2CH_2CH_2CH_2$—) | 109–111° C. | 50 |
| 53. | Trioxane 7gc, formula 7, R = p-Cl—$C_6H_4$, $R_1R_2$ = $CH_2CH_2CH(Ph)CH_2CH_2$—) | 145–148° C. | 24.4 |
| 54. | Trioxane 7gd, formula 7, p-Cl—$C_6H_4$, $R_1R_2$ = $CH_2$—$CH_2$—CH[C($CH_3$)$_2$$CH_2CH_3$]—$CH_2CH_2$— | 115–118° C. | 35.3 |
| 55. | 3-Ethyl-3-methyl-6-[(4'-chloro-[1,1'-biphenyl]-4yl)vinyl]-1,2,4-trioxane (7ge, formula 7, R = p-Cl—$C_6H_4$, $R_1$, $R_2$ = $CH_3$, $CH_2CH_3$) | 70–72° C. | 67.7 |
| 56. | Trioxane belonging to norcamphor group (8g, R = p-Cl—$C_6H_4$) | 122–124° C. | 64.6 |
| 57. | Trioxane belonging to adamantane group (9g, R = p-Cl—$C_6H_4$) | 112–115° C. | 69.14 |

Antimalarial Activity

The antimalarial activity of the test compounds was evaluated in rodent using multidrug resistant strain of *Plasmodium yoelii Nigeriensis* in swiss mice.

General Procedure

Random bred swiss mice of either sex (20±2 gm) were inoculated intraperitoneally with $1 \times 10^5$ *P. yoelii* (MDR) parasites on day zero. The treatments with test compounds were administered to group of 5 mice each at different dose levels ranging between 24–96 mg/kg/day. The treatment was administered via intramuscular route for 4 consecutive days (day 0–3).

Blood smears from experimental mice were observed on day 4 and 7, day 10 and thereafter at regular intervals till day 28 or death of the animal. The parasitaemia level on day 4 was compared with the vehicle control group and the present suppression of parasitaemia in treated groups was calculated.

For determining the curative dose of a compound the treated mice were observed till day 28. The dose at which no parasitaemia develop during the observation period has been reported as the curative dose. The anti-malarial data is summarized in table 7.

TABLE 7

ANTIMALARIAL ACTIVITY OF TRIOXANES AGAINST *P. yoelii* IN MICE

| Compd. No. | Route | Dose Mg/kg | No. Of Animals | % Suppression on Day 4 | Cured/ treated |
|---|---|---|---|---|---|
| 7aa | i.m. | 96 | 5 | 100 | 0/5 |
|  | oral | 96 | 5 | 100 | 5/5 |
| 7ab | i.m. | 96 | 5 | 77.56 | 0/5 |
|  | oral | 96 | 5 | 100 | 0/5 |
| 7ac | i.m. | 96 | 5 | 84.94 | 0/5 |
|  | oral | 96 | 5 | 100 | 5/5 |
| 7ad | i.m. | 96 | 5 | 48 | 0/5 |
|  | oral | 96 | 5 | 88.68 | 0/5 |
| 7ae | i.m. | 96 | 5 | 43.58 | 0/5 |
|  | oral | 96 | 5 | 100 | 0/5 |
| 7ba | i.m. | 96 | 5 | 71.26 | 0/5 |
|  | oral | 96 | 5 | 100 | 0/5 |
| 7bc | i.m. | 96 | 5 | 41.98 | 0/5 |
|  | oral | 96 | 5 | 95.64 | 0/5 |
| 7bd | i.m. | 96 | 5 | 71.73 | 0/5 |
|  | oral | 96 | 5 | 100 | 5/5 |
| 7be | i.m. | 96 | 5 | 91.6 | 0/5 |
|  | oral | 48 | 5 | 100 | 5/5 |
| 7bf | i.m. | 96 | 5 | 71.26 | 0/5 |
|  | oral | 96 | 5 | 100 | 0/5 |
| 7bh | i.m. | 96 | 4 | 100 | 1/4 |
|  | oral | 96 | 4 | 100 | 4/4 |
| 7bi | i.m. | 96 | 5 | 53.01 | 0/5 |
|  | oral | 96 | 5 | 100 | 5/5 |
| 7ca | i.m. | 96 | 5 | 62.18 | 0/5 |
|  | oral | 96 | 5 | 100 | 1/5 |
| 7cb | i.m. | 96 | 5 | 86.31 | 0/5 |
|  | oral | 96 | 5 | 100 | 5/5 |
| 7cd | i.m. | 96 | 5 | 58.17 | 0/5 |
|  | oral | 96 | 5 | 100 | 2/5 |
| 7db | i.m. | 96 | 5 | 9.5 | 0/5 |
|  | oral | 96 | 5 | 100 | 5/5 |
| 7dd | i.m. | 96 | 5 | 73.81 | 0/5 |
|  | oral | 96 | 5 | 100 | 4/5 |
| 7de | i.m. | 96 | 5 | 57.4 | 0/5 |
|  | oral | 96 | 5 | 100 | 3/5 |
| 7df | i.m. | 96 | 5 | 0 | 0/5 |
|  | oral | 96 | 5 | 100 | 3/5 |
| 7eb | i.m. | 96 | 6 | 100 | 6/6 |
|  | oral | 96 | 5 | 100 | 0/5 |
| 7ec | i.m. | 96 | 4 | 100 | 0/4 |
|  | oral | 96 | 4 | 100 | 4/4 |
| 7ee | i.m. | 96 | 5 | 60.9 | 0/5 |
|  | oral | 96 | 5 | 96.8 | 0/5 |
| 7ef | i.m. | 96 | 5 | 42.7 | 0/5 |
|  | oral | 96 | 5 | 100 | 2/5 |
| 7eg | i.m. | 96 | 5 | 87.6 | 0/5 |
|  | oral | 96 | 5 | 100 | 3/5 |
| 7eh | i.m. | 96 | 5 | 92 | 0/5 |
|  | oral | 96 | 5 | 100 | 4/5 |
| 7fa | i.m. | 96 | 5 | 83.7 | 0/5 |
|  | oral | 96 | 5 | died | — |
| 7fb | i.m. | 96 | 4 | 51.41 | 0/5 |
|  | oral | 96 | 4 | 100 | 0/5 |
| 7fc | i.m. | 96 | 5 | 46.4 | 1/5 |
|  | oral | 96 | 5 | 100 | 5/5 |
| 7fd | i.m. | 48 | 5 | 51.09 | 0/5 |
|  | oral | 96 | 5 | 88.39 | 0/5 |
| 7fe | i.m. | 96 | 4 | 89.4 | 0/5 |
|  | oral | 96 | 4 | 100 | 3/5 |
| 7ff | i.m. | 96 | 4 | 46.1 | 0/5 |
|  | oral | 96 | 4 | 100 | 2/5 |
| 8a | i.m. | 96 | 5 | 81.23 | 0/5 |
|  | oral | 96 | 5 | 100 | 5/5 |
| 8b | i.m. | 96 | 5 | 100 | 3/5 |
|  | oral | 48 | 6 | 100 | 6/6 |
| 8c | i.m. | 96 | 5 | 43.55 | 0/5 |
|  | oral | 96 | 5 | 100 | 3/5 |
| 8e | i.m. | 96 | 4 | 100 | 1/4 |
|  | oral | 96 | 4 | 100 | 4/4 |

TABLE 7-continued

ANTIMALARIAL ACTIVITY OF TRIOXANES AGAINST P. yoelii IN MICE

| Compd. No. | Route | Dose Mg/kg | No. Of Animals | % Suppression on Day 4 | Cured/ treated |
|---|---|---|---|---|---|
| 8f | i.m. | 96 | 5 | 100 | 0/5 |
|  | oral | 96 | 5 | 100 | 5/5 |
| 9a | i.m. | 96 | 5 | 81.23 | 0/5 |
|  | oral | 96 | 5 | 100 | 5/5 |
| 9b | i.m. | 96 | 5 | 82.16 | 0/5 |
|  | oral | 96 | 5 | 100 | 5/5 |
| 9c | i.m. | 96 | 5 | 74.57 | 0/5 |
|  | oral | 96 | 5 | 100 | 5/5 |
| 9d | i.m. | 96 | 5 | 60.12 | 0/5 |
|  | oral | 96 | 5 | 100 | 5/5 |
| 9e | i.m. | 96 | 6 | 100 | 0/6 |
|  | oral | 96 | 6 | 100 | 6/6 |
| 9f | i.m. | 96 | 5 | 92.4 | 2/5 |
|  | oral | 48 | 5 | 100 | 5/5 |
| 9g | i.m. | 96 | 5 | 100 | — |
|  | oral | 96 | 5 | 100 | 3/5 |

7aa $R_1 = R_2 =$ —CH$_2$CH$_2$CH$_2$CH$_2$—
7ab $R_1 = R_2 =$ —CH$_2$CH$_2$CH(Ph)CH$_2$CH$_2$—
7ac $R_1 = R_2 =$ —CH$_2$CH$_2$CH$_2$CH$_2$CH$_2$—
7ad $R_1 = R_2 =$ —CH$_2$CH$_2$CH$_2$CH$_2$CH$_2$CH$_2$—
7ae $R_1 = R_2 =$ —CH$_2$—CH$_2$—CH[C(CH$_3$)$_2$CH$_2$CH$_3$]—CH$_2$CH$_2$—

7ba $R_1 = R_2 = CH_3$
7bb $R_1 = CH_3$; $R_2 =$ —CH$_2$-(—CH$_2$)$_8$—CH$_3$
7bc $R_1 = H$; $R_2 =$ phenyl
7bd $R_1 = R_2 =$ —CH$_2$CH$_2$CH$_2$CH$_2$CH$_2$—
7be $R_1 = R_2 =$ —CH$_2$CH$_2$—CH(Ph)—CH$_2$CH$_2$—
7bf $R_1 = CH_3$; $R_2 =$ —CH$_2$CH$_3$
7bg $R_1 = CH_3$; $R_2 =$ —CH$_2$CH$_2$CH$_3$
7bh $R_1 = R_2 =$ —CH$_2$CH$_2$CH$_2$CH$_2$—
7hi $R_1 = R_2 =$ —CH$_2$—CH$_2$—CH[C(CH$_3$)$_2$CH$_2$CH$_3$]—CH$_2$CH$_2$—

7ca $R_1 = R_2 =$ —CH$_2$—CH$_2$—CH$_2$—CH$_2$—CH$_2$—
7cb $R_1 = R_2 =$ —CH$_2$—CH$_2$—CH[C(CH$_3$)$_2$CH$_2$CH$_3$]—CH$_2$CH$_2$—
7cc $R_1 = R_2 =$ —CH$_2$—CH$_2$—CH$_2$—CH$_2$—
7cd $R_1 = R_2 =$ —CH$_2$CH$_2$—CH(Ph)—CH$_2$CH$_2$—

7da $R_1 = CH_3$; $R_2 =$ —CH$_2$CH$_3$
7db $R_1 = R_2 =$ —CH$_2$—CH$_2$—CH$_2$—CH$_2$—CH$_2$—
7dc $R_1 = R_2 =$ —CH$_2$—CH$_2$—CH$_2$—CH$_2$—CH$_2$CH$_2$-
7dd $R_1 = R_2 =$ —CH$_2$CH$_2$CH(Ph)CH$_2$CH$_2$—
7de $R_1 = R_2 =$ —CH$_2$CH$_2$CH$_2$CH$_2$—
7df $R_1 = R_2 =$ —CH$_2$—CH$_2$—CH[C(CH$_3$)$_2$CH$_2$CH$_3$]—CH$_2$CH$_2$—

7ea $R_1 = H$; $R_2 =$ phenyl
7eb $R_1 = R_2 =$ —CH$_2$CH$_2$CH$_2$CH$_2$-
7ec $R_1 = R_2 =$ —CH$_2$CH$_2$CH$_2$CH$_2$CH$_2$-
7ed $R_1 = R_2 = CH_3$, —CH$_2$-(—CH$_2$)$_8$—CH$_3$
7ee $R_1 = R_2 = CH_3$
7ef $R_1 = R_2 =$ —CH$_2$CH$_2$CH(Ph)CH$_2$CH$_2$—
7eg $R_1 = R_2 =$ —CH$_2$—CH$_2$—CH[C(CH$_3$)$_2$CH$_2$CH$_3$]—CH$_2$CH$_2$—
7eh $R_1 = R_2 =$ —CH$_2$CH$_2$CH$_2$CH$_2$CH$_2$CH$_2$-

-continued

7fa R₁, = R₂ = CH₃
7fb R₁ = CH₃; R₂ = —CH₂CH₃
7fc R₁ = R₂ = —CH₂CH₂CH₂CH₂CH₂—
7fd R₁ = R₂ = —CH₂—CH₂—CH[C(CH₃)₂CH₂CH₃]—CH₂CH₂—
7fe R₁ = R₂ = —CH₂CH₂CH₂CH₂—
7ff R₁ = R₂ = —CH₂CH₂—CH(Ph)—CH₂CH₂—

7ga R₁ = R₂ = —CH₂CH₂CH₂CH₂—
7gb R₁ = R₂ = —CH₂CH₂CH₂CH₂CH₂—
7gc R₁ = R₂ = —CH₂CH₂—CH(Ph)—CH₂CH₂—
7gd R₁ = R₂ = —CH₂—CH₂—CH[C(CH₃)₂CH₂CH₃]—CH₂CH₂—
7ge R₁ = CH₃: R₂ = —CH₂CH₃

8a R = cyclopentyl
8b R = cyclohexyl
8c R = cycloheptyl
8d R = cyclooctyl
8e R = Phenyl
8f R = 4-Br-Phenyl
8g R = 4-Cl-Phenyl

9a R = cyclopentyl
9b R = cyclohexyl
9c R = cycloheptyl
9d R = cyclooctyl
9e R = Phenyl
9f R = 4-Br-Phenyl
9g R = 4-Cl-Phenyl

What is claimed is:

1. Substituted 1,2,4-trioxanes of formula 7 having antimalarial activity, wherein R represents cycloalkyl groups selected from the groups consisting of cyclopentyl, cyclohexyl, cycloheptyl and cyclooctyl or aryl groups selected from phenyl, 4-bromophenyl and 4-chlorophenyl, R₁ and R₂ represent hydrogen, alkyl group selected from methyl, ethyl, propyl and decyl, aryl selected from phenyl, or part of a cyclic system such as cyclopentane, cyclohexane, substituted cyclohexane, cycloheptane, cyclo (2.2.1)heptane, adamantane.

2. Substituted 1,2,4-trioxanes as claimed in claim 1, having the structural formulae 7aa–ae as shown below:

7aa R₁=R₂=—CH₂CH₂CH₂CH₂
7ab R₁=R₂=—CH₂CH₂CH(Ph)CH₂CH₂—
7ac R₁=R₂=—CH₂CH₂CH₂CH₂CH₂-
7ad R₁=R₂=—CH₂CH₂CH₂CH₂CH₂CH₂-
7ae R₁=R₂=—CH₂—CH₂—CH[C(CH₃)₂CH₂CH₃]—CH₂CH₂—.

3. Substituted 1,2,4-trioxanes as claimed in claim 1, having the structural formulae 7ba–bi as shown below:

7ba R₁=R₂=CH₃
7bb R₁=CH₃; R₂=—CH₂.(—CH₂)₈—CH₃
7bc R₁=H; R₂=phenyl
7bd R₁=R₂=—CH₂CH₂CH₂CH₂CH₂—
7be R₁=R₂=—CH₂CH₂—CH(Ph)—CH₂CH₂—
7bf R₁=CH₃, R₂=, CH₂CH₃
7bg R₁=CH₃, R₂=—CH₂CH₂CH₃
7bh R₁=R₂=—CH₂CH₂CH₂CH₂—
7bi R₁=R₂=—CH₂—CH₂—CH[C(CH₃)₂CH₂CH₃]—CH₂CH₂—.

4. Substituted 1,2,4-trioxanes as claimed in claim 1, having the structural formulae 7ca–cd as shown below:

7ca R₁=R₂=—CH₂—CH₂—CH₂—CH₂—CH₂—
7cb R₁=R₂=—CH₂—CH₂—CH[C(CH₃)₂CH₂CH₃]—CH₂CH₂—
7cc R₁=R₂=—CH₂—CH₂—CH₂—CH₂—
7cd R₁=R₂=—CH₂CH₂—CH(Ph)—CH₂CH₂—.

5. Substituted 1,2,4-trioxanes as claimed in claim 1, having the structural formulae 7da–df as shown below:

7da $R_1=CH_3, R_2=-CH_2CH_3$
7db $R_1=R_2=-CH_2-CH_2-CH_2-CH_2-CH_2-$
7dc $R_1=R_2=-CH_2-CH_2-CH_2-CH_2-CH_2-CH_2-$
7dd $R_1=R_2=-CH_2-CH_2CH(Ph)-CH_2-CH_2-$
7de $R_1=R_2=-CH_2CH_2CH_2CH_2-$
7df $R_1=R_2=CH_2-CH_2CH[C(CH_3)_2CH_2CH_3]-CH_2CH_2-$.

6. Substituted 1,2,4-trioxanes as claimed in claim 1, having the structural formulae 7ea–eh as shown below:

7ea $R_1=H$; $R_2$=phenyl
7eb $R_1=R_2=-CH_2CH_2CH_2CH_2$-
7ec $R_1=R_2=-CH_2CH_2CH_2CH_2CH_2$
7ed $R_1=CH_3$, $R_2=-CH_2-(-CH_2)_8-CH_2-$
7ee $R_1=R_2=CH_3$
7ef $R_1=R_2=-CH_2CH_2CH(Ph)CH_2CH_2-$
7eg $R_1=R_2=-CH_2-CH_2-CH[C(CH_3)_2CH_2CH_3]-CH_2CH_2-$
7eh $R_1=R_2=-CH_2CH_2CH_2CH_2CH_2CH_2-$.

7. Substituted 1,2,4-trioxanes as claimed in claim 1, having the structural formulae 7fa–ff as shown below:

7fa $R_1=R_2=CH_3$
7fb $R_1=CH_3$, $R_2=CH_2CH_3$
7fc $R_1=R_2=-CH_2CH_2CH_2CH_2CH_2-$
7fd $R_1=R_2-CH_2-CH_2-CH[C(CH_3)_2CH_2CH_3]-CH_2CH_2-$
7fe $R_1=R_2=-CH_2CH_2CH_2CH_2-$
7ff $R_1=R_2=-CH_2CH_2-CH(Ph)-CH_2CH_2-$.

8. Substituted 1,2,4-trioxanes as claimed in claim 1, having the structural formulae 7ga–ge as shown below:

7ga $R_1=R_2=-CH_2CH_2CH_2CH_2-$
7gb $R_1=R_2=-CH_2CH_2CH_2CH_2CH_2-$
7gc $R_1=R_2=-CH_2CH_2-CH(Ph)-CH_2CH_2-$
7gd $R_1=R_2=-CH_2-CH_2-CH[C(CH_3)_2CH_2CH_3]-CH_2CH_2-$
7ge $R_1=CH_3$; $R_2=-CH_2CH_3$.

9. Substituted 1,2,4-trioxanes as claimed in claim 1, having the structural formulae 8a–g as shown below:

8a R=cyclopentyl
8b R=cyclohexyl
8c R=cycloheptyl
8d R=cyclooctyl
8e R=Phenyl
8f R=4-Br-Phenyl
8g R=4-Cl-Phenyl.

10. Substituted 1,2,4-trioxanes as claimed in claim 1, having the structural formulae 9a–g as shown below:

9a R=cyclopentyl
9b R=cyclohexyl
9c R=cycloheptyl
9d R=cyclooctyl
9e R=Phenyl
9f R=4-Br-Phenyl
9g R=4-Cl-Phenyl.

11. A method of treating a subject having malaria, comprising administering to said subject having malaria, a pharmaceutically effective dosage of a substituted 1,2,4-trioxane of formula 7 having antimalarial activity, wherein R represents cycloalkyl groups selected from the groups consisting of cyclopentyl, cyclohexyl, cycloheptyl and cyclooctyl or aryl groups selected from phenyl, 4-bromophenyl and 4-chlorophenyl, $R_1$ and $R_2$ represent hydrogen, alkyl group selected from methyl, ethyl, propyl and decyl, aryl selected from phenyl, or part of a cyclic system such as cyclopentane, cyclohexane, substituted cyclohexane, cycloheptane, cyclo(2.2.1)heptane, adamantane and a pharmaceutically acceptable carrier.

12. The method as claimed in claim 11 wherein the composition is administered intramuscularly or orally.

13. The method as claimed in claim 11 wherein the subject is swiss mice.

* * * * *